United States Patent [19]

Inagaki et al.

[11] Patent Number: 4,612,277

[45] Date of Patent: * Sep. 16, 1986

[54] IMAGE-RECEIVING ELEMENT FOR SILVER SALT DIFFUSION PROCESS WITH IMAGE STABILIZER PRECURSOR

[75] Inventors: Yoshio Inagaki; Katsusuke Endo, both of Kanagawa, Japan

[73] Assignee: Fuji Photo Film Co., Ltd., Kanagawa, Japan

[*] Notice: The portion of the term of this patent subsequent to Sep. 18, 2001 has been disclaimed.

[21] Appl. No.: 629,851

[22] Filed: Jul. 11, 1984

[30] Foreign Application Priority Data

Jul. 11, 1983 [JP] Japan .................. 58-125645

[51] Int. Cl.$^4$ .................. G03C 5/54; G03C 1/02
[52] U.S. Cl. .................. 430/233; 430/248; 430/428; 430/955; 430/611
[58] Field of Search .............. 430/233, 248, 428, 611, 430/955

[56] References Cited

U.S. PATENT DOCUMENTS

| | | | |
|---|---|---|---|
| 3,655,380 | 4/1972 | Parsons | 430/233 |
| 3,704,126 | 11/1972 | Land et al. | 430/233 |
| 3,963,495 | 6/1976 | Kato et al. | 430/233 |
| 4,279,983 | 7/1981 | Bilofsky et al. | 430/233 |
| 4,307,175 | 12/1981 | Pollet et al. | 430/611 |
| 4,390,613 | 6/1983 | Mehta et al. | 430/219 |
| 4,472,493 | 9/1984 | Okamura et al. | 430/219 |

*Primary Examiner*—Richard L. Schilling
*Attorney, Agent, or Firm*—Sughrue, Mion, Zinn, Macpeak & Seas

[57] ABSTRACT

An image-receiving element for a silver salt diffusion transfer process is disclosed, wherein the element comprises an image stabilizing agent precursor having an inactive group capable of being removed upon contact with an alkaline processing composition.

28 Claims, No Drawings

IMAGE-RECEIVING ELEMENT FOR SILVER SALT DIFFUSION PROCESS WITH IMAGE STABILIZER PRECURSOR

FIELD OF THE INVENTION

This invention relates to a photographic element for use in a silver salt diffusion transfer process.

BACKGROUND OF THE INVENTION

A diffusion transfer photographic process utilizing a silver salt such as a silver halide is hitherto known, which comprises superimposing a photosensitive element containing an exposed silver halide photographic emulsion on an image-receiving element containing a silver precipitating agent, and coating the opposing surfaces of the two elements with an alkaline processing solution containing a solvent for the silver halide in the presence of a developing agent, thereby forming a positive silver image directly on the image-receiving element. In this method, the unexposed silver halide emulsion in the photosensitive element is dissolved by the solvent for the silver halide and moves to the alkaline processing solution in a form of silver ion complex. Consequently, the silver ion complex is transferred to the image-receiving element and by the action of the silver precipitating agent, is precipitated in the image-receiving element as a silver image. A positive image is thus directly formed.

The image-receiving element used in this method is usually produced by providing an image-receiving layer containing a silver precipitating agent selected from metal sulfides such as nickel sulfide, silver sulfide and palladium sulfide or noble metal colloids such as gold, silver and palladium colloids in an alkali-permeable polymer binder selected from gelatin, carboxy methyl cellulose, hydroxyethyl cellulose, regenerated cellulose, polyvinyl alcohol, sodium alginate, starch, gum arabic and colloidal silica on a paper support such as baryta paper, polyethylene laminated paper, lacquered paper or a synthetic paper-like sheet or a film support such as an acetylcellulose film, a polyethylene terephthalate film or a polystyrene film.

Many attempts have been made to improve such image-forming elements, including inventions directed to the use of regenerated cellulose as a binder for the image-receiving layer.

U.S. Pat. No. 3,179,517 discloses a method of preparing an image-receiving element which comprises hydrolyzing an acetyl cellulose film in the presence of alkali to form a layer of regenerated cellulose, dipping the regenerated cellulose layer in a gold salt solution and a solution of a reducing agent, and thus reacting them in the regenerated cellulose layer to form a silver precipitating agent composed of gold colloid. Japanese Patent Publication No. 32754/69 (corresponding to U.S. Pat. No. 3,671,241) discloses an image-receiving element prepared by including a silver precipitating agent into an alkali-impermeable polymeric substance by vacuum deposition, dissolving it in a solvent capable of dissolving the polymeric substance, coating the solution on a support, drying the coated support and hydrolyzing the surface layer of the resulting polymeric layer to make it alkali-permeable.

Japanese Patent Publication No. 43944/71 (corresponding to U.S. Pat. No. 3,772,025) describes a method of preparing an image-receiving element which comprises forming a silver precipitating agent in an acetyl cellulose solution, coating the solution on a support, and thereafter hydrolyzing the acetyl cellulose to form a regenerated cellulose.

Japanese Patent Publication No. 49411/76 describes an image-receiving element prepared by hydrolyzing a cellulose ester layer, and including a silver precipitating agent into the hydrolyzed layer simultaneously with or after the hydrolysis.

U.S. Pat. No. 4,163,816 describes an image-receiving element prepared by hydrolyzing acetyl cellulose with an acid in solution to convert it into acetyl cellulose of a low degree of acetylation, and coating the resulting solution on a support.

The image-receiving elements obtained by these prior techniques, however, have the disadvantage that silver images formed on these elements are susceptible to discoloration or fading.

Attempts to improve this disadvantage are disclosed in U.S. Pat. No. 3,533,789, Japanese Patent Publication No. 5392/71 (corresponding to U.S. Pat. No. 3,533,789), and British Patent No. 1,164,642 which relate to a method involving coating a water-soluble polymer solution containing an alkali neutralizing component on the surface of image-receiving element forming a silver image. According to this method, a considerable period of time is required until the surface coated with the aqueous polymer solution completely dries. During this time, the surface is sticky and one element cannot be put upon another. Moreover, fingerprints or dust frequently adhere to the surface, and the additional step of coating of such a solution on the silver image is required.

Japanese Patent Publication No. 44418/81 (corresponding to U.S. Pat. No. 3,607,269) discloses an image-receiving element comprising a support and formed thereon (I) a cellulose ester, polyvinyl ester or polyvinyl acetyl layer which is hydrolyzable and becomes alkali-permeable upon hydrolysis and contains a compound capable of diffusing and changing the nature of a silver image and (II) a regenerated cellulose layer containing a silver precipitating agent, in this sequence. It describes organic mercapto compounds as the compound capable of diffusing and changing the nature of the silver image. With this image-receiving element, the mercapto compound in layer I gradually diffuses into layer II after the diffusion transfer treatment, and thus protects the silver image formed in layer II and prevents its discoloration or fading.

In order for the above image-receiving element to completely prevent discoloration or fading, the mercapto compound must have a sufficient ability to prevent discoloration or fading; stay in layer I during the storage of the undeveloped image-receiving layer and the diffusion transfer treatment; permeate from layer I to layer II after the formation of a silver image by the diffusion transfer treatment and thus protect the image formed in the layer II. If the diffusion of the mercapto compound from layer I to layer II occurs before the completion of the diffusion transfer treatment, development is inhibited and the optical density of the transferred silver image on the image-receiving element is decreased. Furthermore, if the diffusion of the mercapto compound is too slow, discoloration or fading of the silver image occurs before it is protected by the mercapto compound.

The mercapto compounds described in Japanese Patent Publication No. 44418/81 have the defect that their ability to prevent discoloration or fading is insufficient and consequently the image undergoes discoloration or fading, and the further disadvantage that during storage of undeveloped image-receiving elements, the mercapto compounds diffuse from the layer I to the layer II to inhibit development and reduce the optical density of the transferred silver image.

Japanese Patent Application (OPI) No. 120634/74 (corresponding to U.S. Pat. No. 3,963,495) (the term "OPI" as used herein refers to a "published, unexamined Japanese patent application"), describes an image-receiving element prepared by using a homopolymer, copolymer or graft copolymer of a monoacrylate or monomethacrylate of a polyhydric alcohol as a polymer layer containing a compound capable of changing the nature of a silver image. The compound described, as is the case with the compounds described in Japanese Patent Publication No. 44418/81 (corresponding to U.S. Pat. No. 3,607,269), has an insufficient ability to prevent the discoloration or fading of images, or causes a decrease in the optical density of the transferred silver image during storage of undeveloped image-receiving elements.

British Patent No. 1,276,961 discloses the use of 2-mercapto-1,3,4-triazole derivatives for obtaining stable silver images by the diffusion transfer process. U.S. Pat. No. 3,655,380 discloses that 5-seleno-1,2,3,4-tetrazole derivatives not only can modify the color of a silver image obtained by a diffusion transfer process to a nutral gray color, but also provide stable silver images. These compounds, however, have the defect that the stabilization of silver image produced by the diffusion transfer process is insufficient, and the images undergo discoloration or fading. It is desired to develop compounds which have a great stabilizing effect on silver images, and which do not adversely affect undeveloped image-receiving elements during storage, and image-receiving elements containing such compounds.

SUMMARY OF THE INVENTION

It is a first object of this invention thereof to provide a novel image-receiving element for a diffusion transfer process.

A second object of this invention is to provide an image-receiving element for a diffusion transfer process which is not deteriorated during storage before development.

A third object of this invention is to provide an image-receiving element in which a silver image obtained by a diffusion transfer process is stable.

A fourth object of this invention is to provide a novel image stabilizing agent which is effective for stabilizing a silver image obtained by a diffusion transfer process and which does not markedly reduce the performance of an image-receiving element during storage before development.

It has now been found that these objects of the invention are achieved by an image-receiving element for a silver salt diffusion transfer process, wherein the element comprising an image-stabilizing agent precursor having an inactive group capable of being removed upon contact with an alkaline processing composition.

DETAILED DESCRIPTION OF THE INVENTION

The image stabilizing agent precursor of the present invention is a compound comprises (A) an inactive group capable of being removed upon contact with an alkaline processing composition and (B) an image stabilizing agent.

Generally, the image stabilizing agent precursor used in this invention substantially lacks the function of stabilizing an image before activation, but has an image stabilizing function after it is activated.

Compounds represented by the following formula (I) are preferred as the image stabilizing agent precursor:

$$(A)_{\overline{n}}B \tag{I}$$

wherein A is a group selected from

R—S— and Ar—S— wherein F represents a non-metal atomic grouping which forms a substituted or unsubstituted heterocyclic ring, R represents a substituted or unsubstituted alkyl group and Ar represents a substituted or unsubstituted aryl group; and B represents an organic group or a metal which is bonded to A at the 1-position of A and is removed when contacted with a processing composition, and n is an integer of 1 to 6. When B is a metal, n is preferably an integer of 2 to 6, more preferably 2 or 3, and most preferably 2. When B is an organic group, n is preferably an integer of 1 to 3, more preferably 1 or 2.

Examples of the metal represented by B include copper, zinc, mercury, tin, nickel, cadmium, cobalt, manganese, calcium and iron (all divalent); chromium, aluminum and titanium (all trivalent); vanadium (pentavalent); and chromium, molybdenum and tungsten (all hexavalent).

Examples of the organic group represented by B are

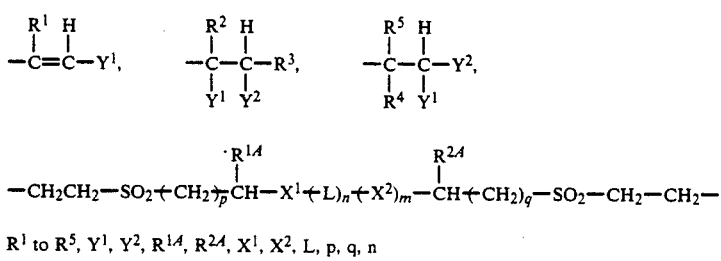

$R^1$ to $R^5$, $Y^1$, $Y^2$, $R^{14}$, $R^{24}$, $X^1$, $X^2$, L, p, q, n and m will be defined hereinafter.

When B is the organic group, preferred image stabilizing agent precursors are compounds represented by the following general formula (II-A), (II-B) or (II-C):

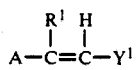
(II-A)

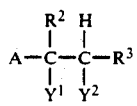
(II-B)

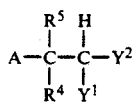
(II-C)

wherein A is as defined for general formula (I); $Y^1$ and $Y^2$ may be the same or different and each represents an electron-attractive group; $R^1$ represents hydrogen, an alkyl group, a substituted alkyl group, an aryl group, a substituted aryl group, a carboxyl group or its ester or salt, a carbamoyl group or an N-substituted carbamoyl group; $R^2$ represents hydrogen, an alkyl group, a substituted alkyl group, an aryl group, or a substituted aryl group; $R^3$ is the same as $Y^1$ or hydrogen, an alkyl group, a substituted alkyl group, an aryl group, a substituted aryl group, or a group of the formula $R^6$—S— wherein $R^6$ represents an alkyl group, a substituted alkyl group, an aryl group, a substituted aryl group or a heterocyclic group (which may be substituted or unsubstituted); $R^4$ represents hydrogen, an aryl group, a substituted aryl group or a heterocyclic group (which may be substituted or unsubstituted); and $R^5$ represents hydrogen, an aryl group, a substituted aryl group or a heterocyclic group (which may be substituted or unsubstituted). Acyl groups including substituted acyl groups are preferred as the electron attracting group represented by $Y^1$ and $Y^2$. Examples are acyl groups derived from aliphatic or aromatic carboxylic acids or sulfonic acids. The acyl groups may be substituted by a halogen atom.

Specific examples of the compounds represented by general formula (II-A), (II-B) and (II-C) are given below, but the present invention should not be construed as being limited thereto.

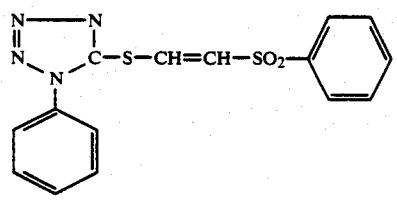
1

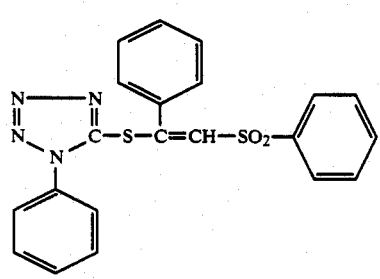
2

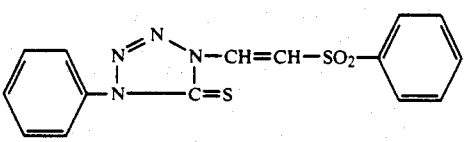
3

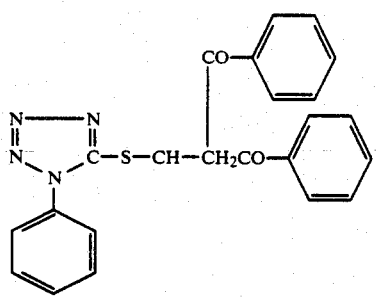
4

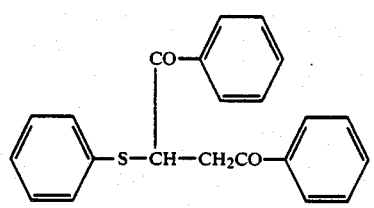
5

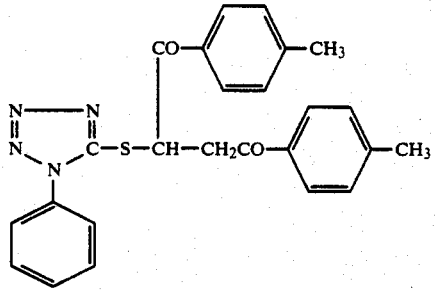
6

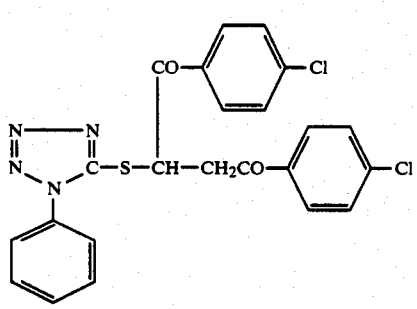
7

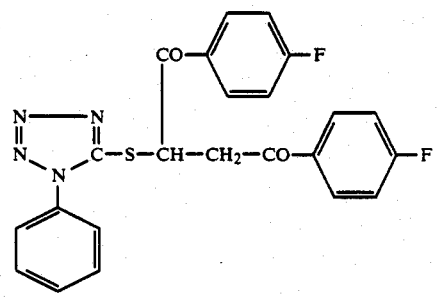
8

-continued
9
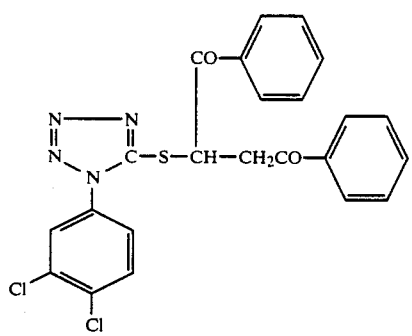
10
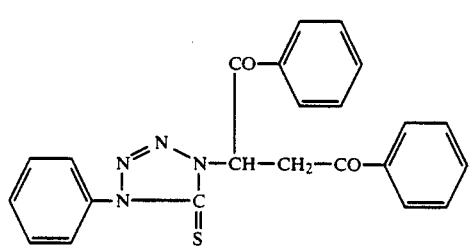
11
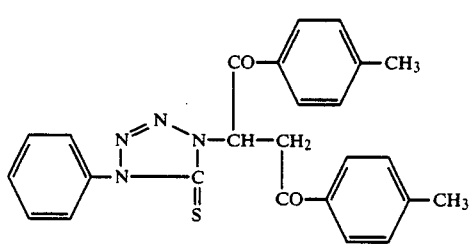
12
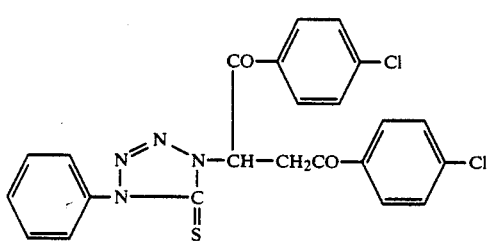
13
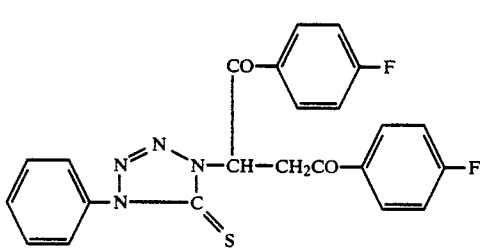
14
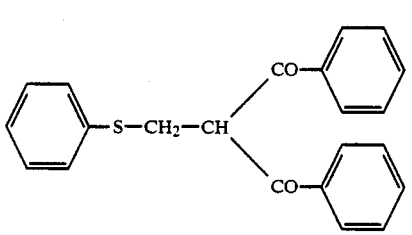
-continued
15
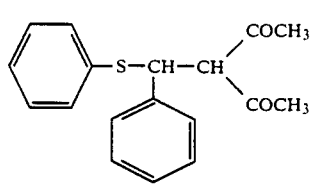
16
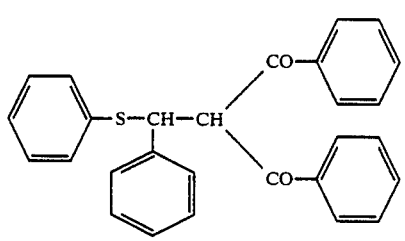
17
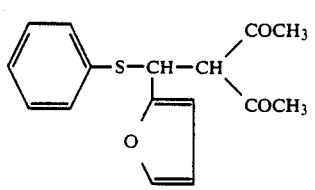
18
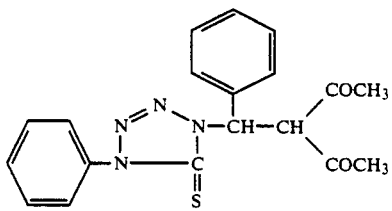
19
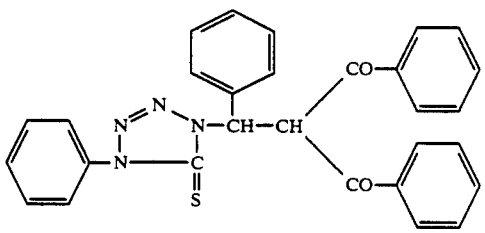
20
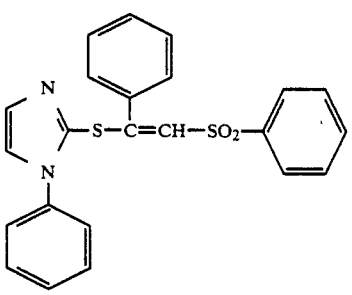

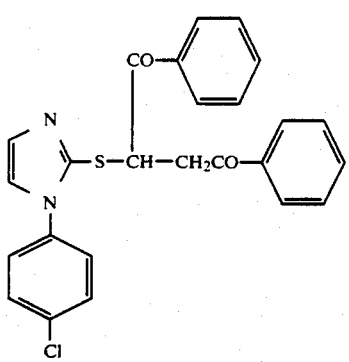

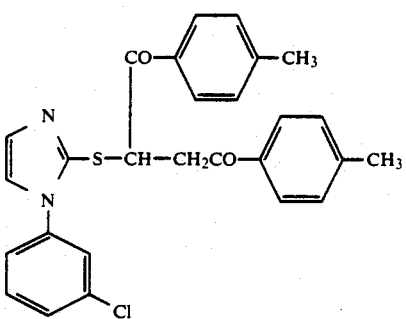

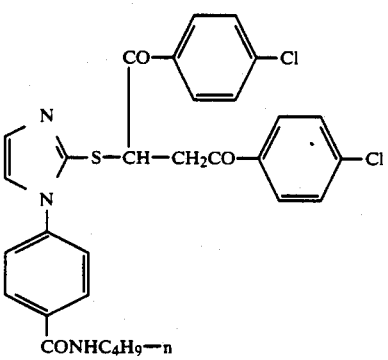

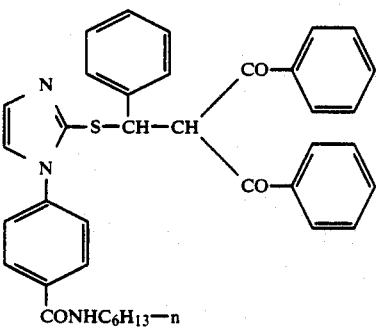

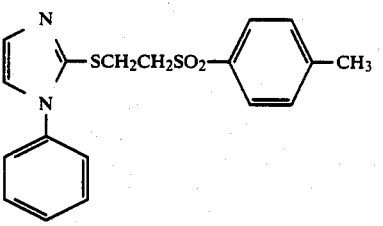

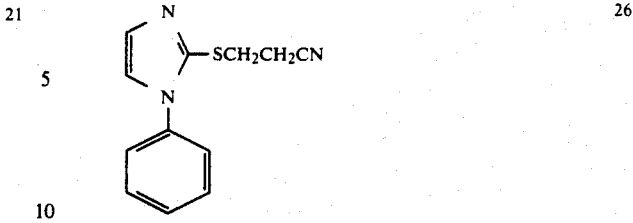

Preferred examples of the compounds represented by general formula (II-A) include Compounds 1, 2, 3 and 20. Particularly preferred example of the compounds represented by general formula (II-A) is Compound 20.

Preferred examples of the compounds represented by general formula (II-B) include Compounds 21, 22 and 23. Particularly preferred example of the compounds represented by general formula (II-B) is Compound 21.

Preferred examples of the compounds represented by general formula (II-C) include Compounds 25 and 26.

The compounds of general formulae (II-A), (II-B) and (II-C) are described in Japanese Patent Application (OPI) No. 77842/81 (corresponding to U.S. Pat. No. 4,307,175) and can be synthesized in accordance with the disclosure of this patent document.

Of the compounds of general formula (I), compounds of the following formula (III) are preferred:

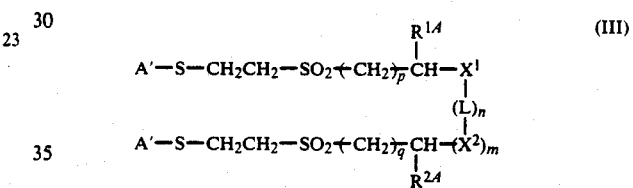

wherein A' represents a substituted or unsubstituted alkyl group, a substituted or unsubstituted aryl group or a 5- or 6-membered nitrogen-containing heterocyclic ring; $R^{1A}$ and $R^{2A}$ may be the same or different and each represents hydrogen or an alkyl group having 1 to 4 carbon atoms; p and q are each 0 or an integer of 1 to 3 and may be the same or different; $X^1$ and $X^2$ may be the same or different, and each represents an ester linkage, a substituted or unsubstituted amido linkage, or an ether linkage and L represents an alkylene group, a phenylene group or a xylylene group; and n and m are each 0 or 1. When $X^1$ and $X^2$ are amido groups, substituents on the nitrogen may be linked to each other to form a hetero ring together with L and a part of each of $X^1$ and $X^2$.

The amido linkage may be a sulfonamido linkage. The hetero ring formed of L and a part of each of $X^1$ and $X^2$ may be substituted or unsubstituted.

Examples of the hetero ring are a perhydrotriazine ring, an imidazoline, a piperazine ring and a perhydropyrimidine ring. The perhydrotriazine ring can be substituted.

The alkyl group represented by A' preferably has 1 to 20 carbon atoms, such as a methyl, ethyl, propyl or octyl group.

Substituents on the alkyl group represented by A' include, for example, an alkoxy group (preferably having 1 to 14 carbon atoms, such as a methoxy or ethoxy group); a nitro group; a halogen atom (such as chlorine); an aryl group (preferably having not more than 14 carbon atoms, such as a phenyl or naphthyl group which may further be substituted by a substituent such as an alkyl group); an alkoxycarbonyl group (with the alkyl moiety preferably having 1 to 14 carbon atoms, such as a methoxycarbonyl or ethoxycarbonyl group); a substituted or unsubstituted carbamoyl group (with the substituent preferably being an alkyl group having 1 to 14 carbon atoms or a phenyl group); a substituted or unsubstituted sulfamoyl group (with the substituent preferably being an alkyl group having 1 to 14 carbon atoms or a phenyl group); a substituted or unsubstituted alkylsulfonyl group (preferably having 1 to 14 carbon atoms); a substituted or unsubstituted arylsulfonyl group (preferably having 6 to 14 carbon atoms); an alkylsulfonamido or aryl sulfonamido group in which (the alkyl or aryl moiety may be further substituted, the nitrogen atom of the sulfonamido group may be further substituted by an alkyl group having not more than 14 carbon atoms, a substituted alkyl group, a cycloalkyl group, a substituted cycloalkyl group, an aryl group, a substituted aryl group, or a 5- or 6-membered substituted or unsubstituted heterocyclic group containing at least one nitrogen, oxygen of sulfur atom); a carbonamido group (the nitrogen atom of the carbonamido group may be substituted by an alkyl group having not more than 14 carbon atoms, a substituted alkyl group, a cycloalkyl group, a substituted cycloalkyl group, an aryl group, a substituted aryl group, or a 5- to 7-membered substituted or unsubstituted heterocyclic group containing at least one nitrogen, oxygen or sulfur atoms); a heterocyclic group, preferably a 5- or 7-membered substituted or unsubstituted alkoxycarbonyl group containing at least one nitrogen, oxygen or sulfur atom; a substituted or unsubstituted alkoxycarbonyl group (preferably having 2 to 14 carbon atoms); a substituted or unsubstituted acyloxy group (preferably having 2 to 14 carbon atoms); a substituted or unsubstituted alkylthio group (preferably having 1 to 14 carbon atoms); a substituted or unsubstituted arylthio group (preferably having 6 to 14 carbon atoms); a secondary or tertiary amino group substituted by an alkyl group having 1 to 14 carbon atoms or an aryl group having 6 to 14 carbon atoms; a primary amino group; a hydroxyl group; a carboyl group; a sulfonic acid group; or a cyano group.

The aryl group represented by A' include, for example, a phenyl group or a naphthyl group.

Substituents on the aryl group represented by A' include, for example, an alkyl group (preferably having 1 to 14 carbon atoms, such as a methyl or ethyl group); an alkoxy group (preferably having 1 to 14 carbon atoms, such as a methoxy or ethoxy group); a nitro group; a halogen atom (such as a chlorine atom); an alkoxycarbonyl group (with the alkyl moiety thereof preferably having 1 to 14 carbon-atoms, such as a methoxycarbonyl or ethoxycarbonyl group); a substituted or unsubstituted carbamoyl group (with the substituent thereof preferably being an alkyl group having 1 to 14 carbon atoms or a phenyl group); a substituted or unsubstituted sulfamoyl group (with the substituent thereof preferably being an alkyl group having 1 to 14 carbon atoms or a phenyl group); a substituted or unsubstituted alkylsulfonyl group (preferably having 1 to 14 carbon atoms); a substituted or unsubstituted arylsulfonyl group (preferably having 6 to 14 carbon atoms); an alkyl sulfonamido or aryl sulfonamido group (in which the alkyl or aryl moiety thereof may be further substituted and the nitrogen atom of the sulfonamido group thereof may be further substituted by an alkyl group having not more than 14 carbon atoms, a substituted alkyl group, a cycloalkyl group, a substituted cycloalkyl group, an aryl group, a substituted aryl group, or a 5- or 6-membered substituted or unsubstituted heterocyclic group having at least one nitrogen, oxygen or sulfur atom); a carbonamido group (in which the nitrogen atom of the carbonamido group may be further substituted by an alkyl group having not more than 14 carbon atoms, a substituted alkyl group, a cycloalkyl group, a substituted cycloalkyl group, an aryl group, a substituted aryl group, or a 5- to 7-membered substituted or unsubstituted heterocyclic group containing at least one nitrogen, oxygen or sulfur atom); a heterocyclic group, preferably a 5- to 7-membered substituted or unsubstituted heterocyclic group containing at least one nitrogen, oxygen or sulfur atom; a substituted or unsubstituted alkoxycarbonyl group (preferably having 2 to 14 carbon atoms); a substituted or unsubstituted acyloxy group (preferably having 2 to 14 carbon atoms); a substituted or unsubstituted alkylthio group (preferably having 1 to 14 carbon atoms); a substituted or unsubstituted arylthio group (preferably having 6 to 14 carbon atoms); a secondary or tertiary amino group further substituted by an alkyl group having 1 to 14 carbon atoms or an aryl group having 6 to 14 carbon atoms; a primary amino group; a hydroxyl group; a carboxyl group, a sulfonic acid group; or a cyano group.

When A' is a nitrogen-containing heterocyclic ring, may be fused with another ring, such as a benzene ring, or be further substituted by a substituent normally used (for example, a methyl group, an n-butyl group, an n-octyl group, a phenyl group, a 3-chlorophenyl group, a 4-hexylcarbamoylphenyl group, a methylthio group and a butylthio group). Examples of the nitrogen-containing heterocyclic group include tetrazole rings e.g., a tetrazole ring or a phenyltetrazole ring; triazole rings, e.g., a benzotriazole ring or a 1,2,4-triazole ring; diazole rings, e.g., a benzimidazole ring or an imidazole; pyrimidine rings; and monoazole rings, e.g., a benzothiazole ring or a benzoxazole ring. Preferably, the nitrogen-containing hetero ring contains at least two hetero atoms, e.g., an imidazole ring.

Preferred compounds of general formula (III) are represented by general formula (IV).

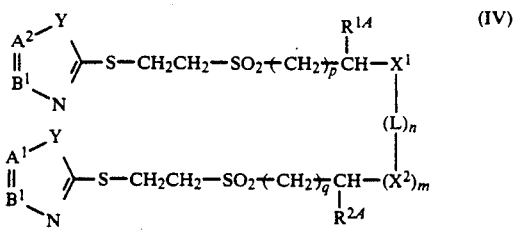

wherein, $A^2$ and $B^1$ may be the same or different and each represents a carbon atom or a nitrogen atom, wherein carbon atom $A^2$ or $B^1$ may be further substituted by a substituent having not more than 20 carbon atoms and when $A^2$ and $B^1$ are both carbon atoms, they may be linked through a divalent group to form an addition ring; Y represents an oxygen atom, a sulfur atom or a group of formula $N—R^O$ in which $R^O$ represents a substituent having not more than 20 carbon atoms; and $R^{14}$, $R^{24}$, $X^1$, $X^2$, m, n, p, q, and L are the same as defined for general formula (III). .

In especially preferred compounds of general formula (IV), R^O represents an alkyl group, an alkoxy-substituted alkyl group, a hydroxyl-substituted alkyl group, a carbamoyl-substituted alkyl group, a carbonamido-substituted alkyl group, a sulfamoyl-substituted alkyl group, a sulfonamido-substituted alkyl group, a phenyl group, each having not more than 15 carbon atoms, an alkoxy-substituted phenyl group, a hydroxyalkyl-substituted phenyl group, a carbamoylsubstituted phenyl group, a carbonamido-substituted phenyl group, a sulfamoyl-substituted phenyl group, a sulfonamido-substituted phenyl group or a halogen-substituted phenyl group, each having not more than 15 carbon atoms; $A^2$ and $B^1$ may be the same or different and each represents a carbon atom or a nitrogen atom, wherein the carbon atom may be further substituted by an alkyl group having not more than 15 carbon atoms, an alkoxy-substituted alkyl group, a hydroxy-substituted alkyl group, a carbamoyl-substituted alkyl group, a carbonamido-substituted alkyl group, a sulfamoyl-substituted alkyl group, a sulfonamido-substituted alkyl group, a phenyl group, an alkyl-substituted phenyl group, an alkoxy-substituted phenyl group, a hydroxyalkyl-substituted phenyl group, a carbamoyl-substituted phenyl group, a carbonamido-substituted phenyl group, a sulfonamido-substituted phenyl group, a sulfamoyl substituted phenyl group, an alkoxy group, an alkylthio group, a hydroxy-substituted alkoxy group, an alkoxy-substituted alkoxy group, a hydroxy-substituted alkylthio group or an alkoxysubstituted alkylthio group; and when $A^2$ and $B^1$ are both carbon atoms, they may be linked to each other through a divalent group to form an additional aromatic ring;

p and q are each 0 or 1; $R^{1A}$ and $R^{2A}$ are each preferably hydrogen or a methyl group;

L is preferably an alkylene group having 1 to 6 carbon atoms (e.g., a methylene, ethylene, trimethylene or hexamethylene group), a phenylene group or a xylylene group; and $X^1$ and $X^2$ are preferably an amido linkage or an ether linkage.

When both $X^1$ and $X^2$ represent an amido linkage, n and m are both preferably 1, and compounds represented by general formula (V) below are especially preferred.

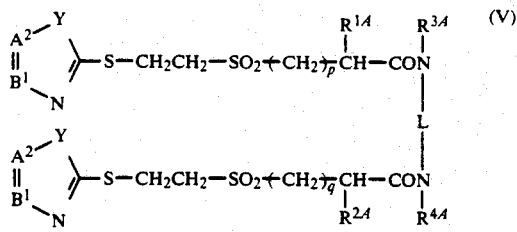

wherein, Y, $A^2$, $B^1$, $R^{1A}$, $R^{2A}$, L, p and q are as defined in general formula (IV). $R^{3A}$ and $R^{4A}$ may be the same or different, and each represents hydrogen, an alkyl group having 1 to 4 carbon atoms (e.g., a methyl, ethyl, isopropyl or butyl group) or a phenyl group. $R^{3A}$ and $R^{4A}$ may be linked to each other to form a hetero ring together with L and the two nitrogen atoms.

Preferred examples of the compounds of formula (V) are those of the following general formula (VI). The above hetero ring may further be substituted, and preferred examples are compounds of general formula (VII) below.

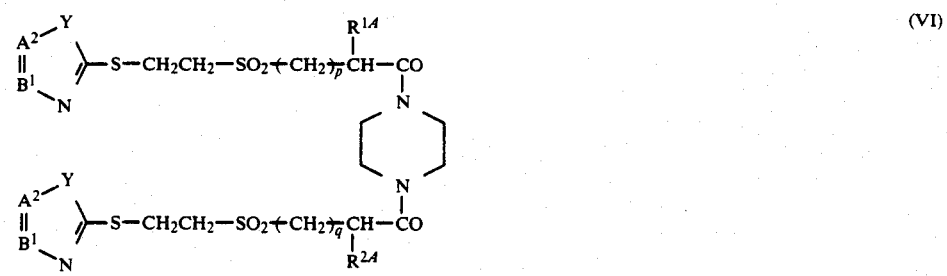

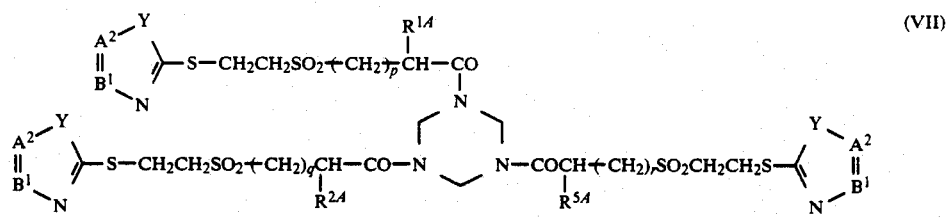

wherein, $A^2$, $B^1$, Y, $R^{1A}$, $R^{2A}$, p and q are as defined in general formula (IV); r is 0 or 1; and $R^{5A}$ represents hydrogen or a methyl group.

When $X^1$ represents an ether linkage, n and m are desirably both 0, and compounds represented by the following general formula (VIII) are especially preferred.

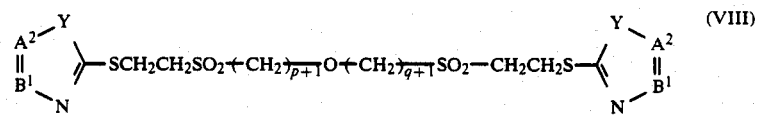

wherein, $A^2$, $B^1$, Y, p and q are as defined in general formula (IV).

In the above general formulae (IV) to (VI) and (VIII), p is preferably equal to q, and in formula (VII), p=q=r.
Specific examples of the nitrogen-containing hetero ring represented by $A^1$ in general formula (III) are shown below, but the present invention is not to be constived as being limited thereto.
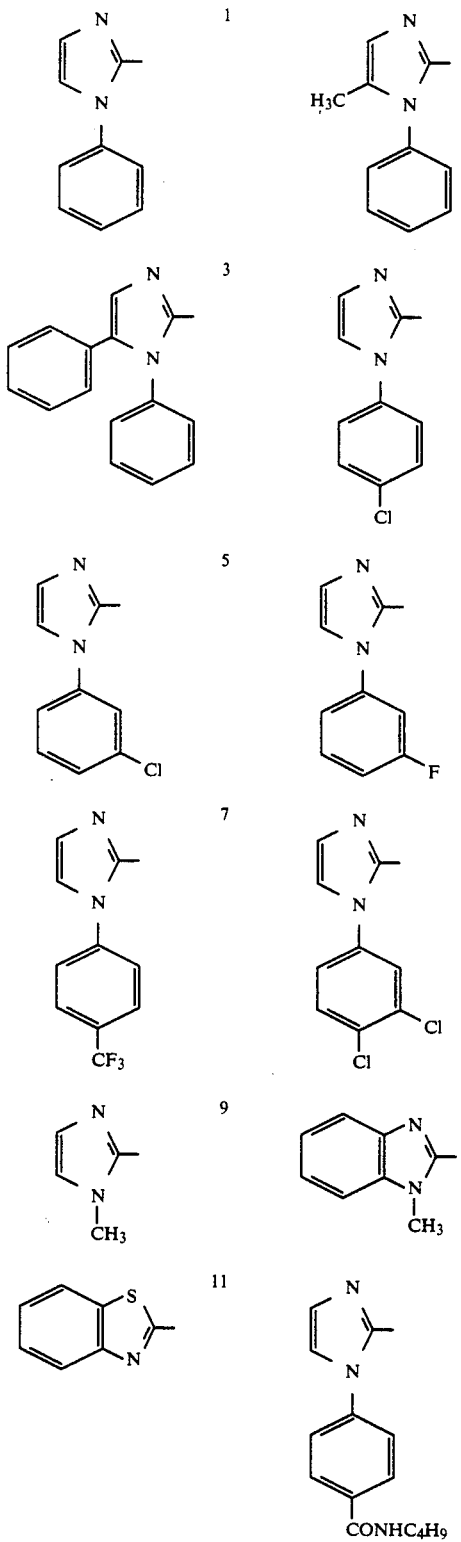
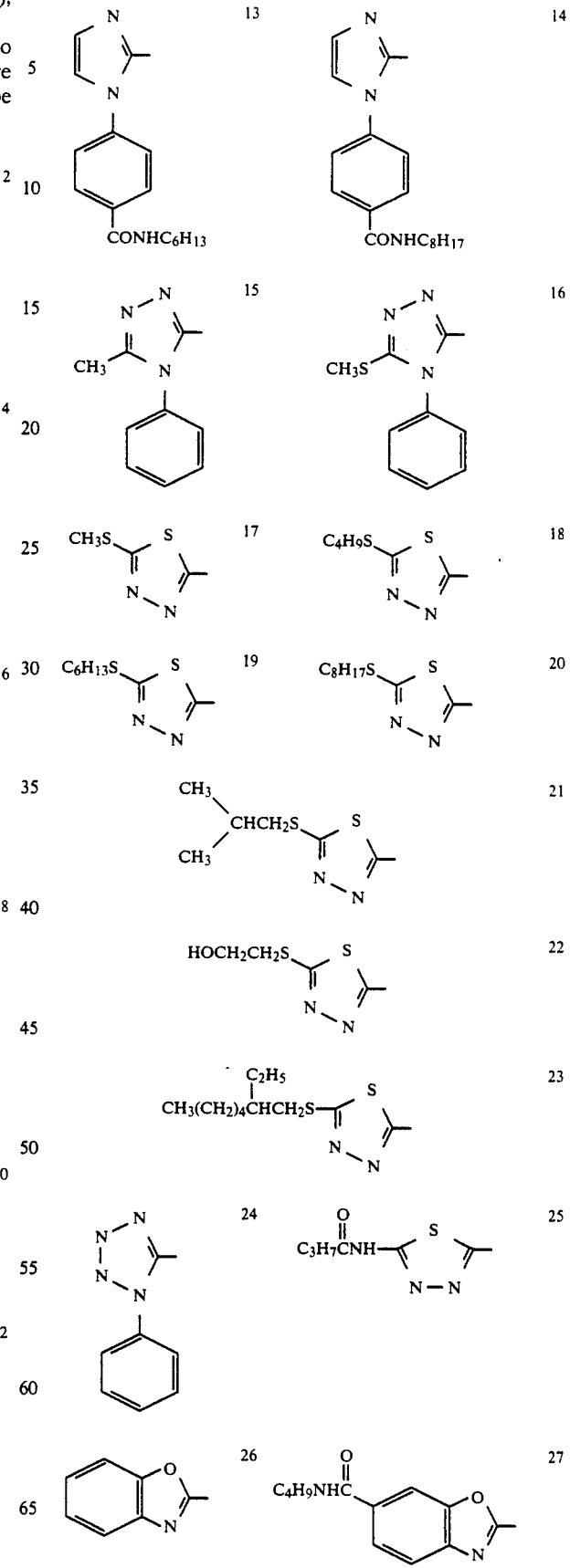

-continued
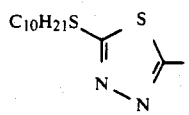 28 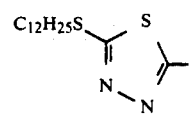 29
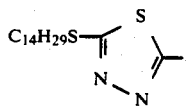
-continued
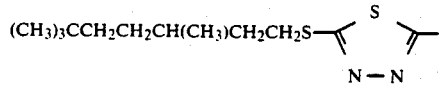 31
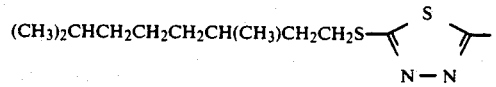 32
Specific examples of the compounds represented by general formula (III) which can be effectively used in the present invention are shown below. However, the present invention is not to be constived as being limited thereto.

27. 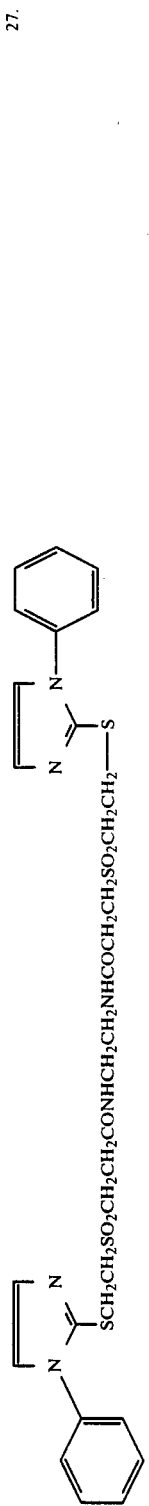
28. 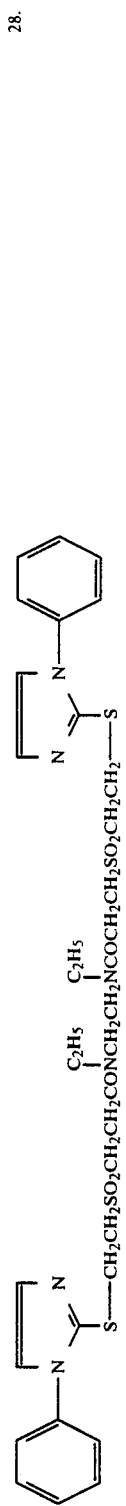
29. 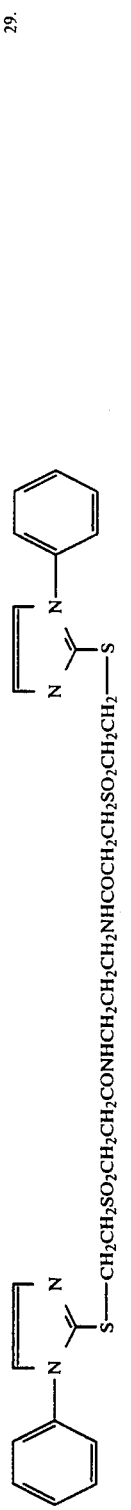
30. 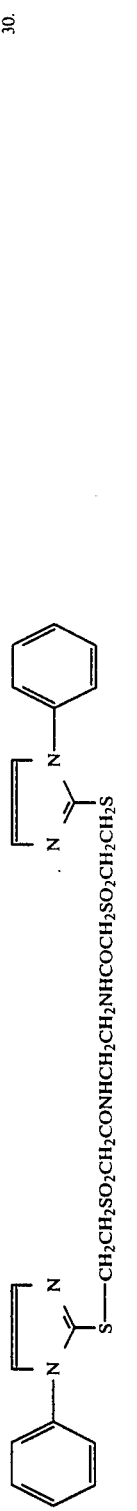
31. 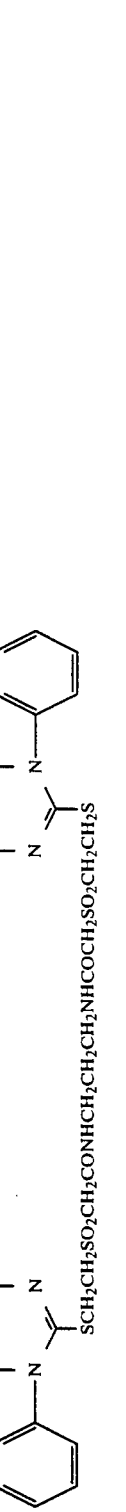
32. 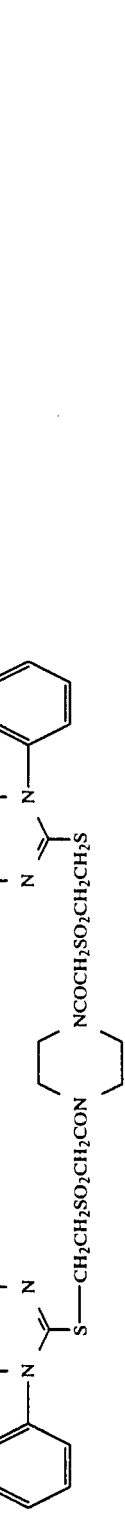

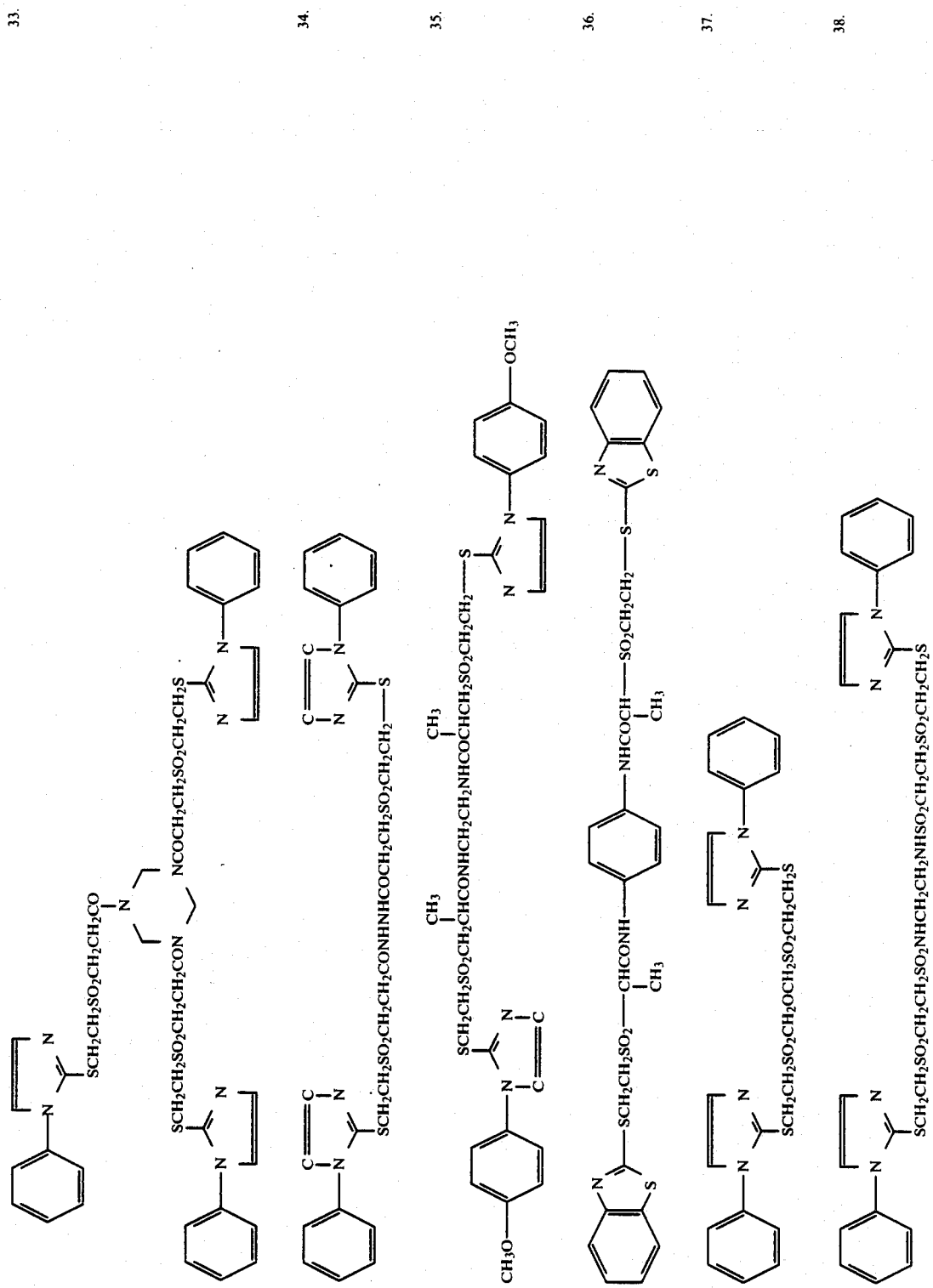

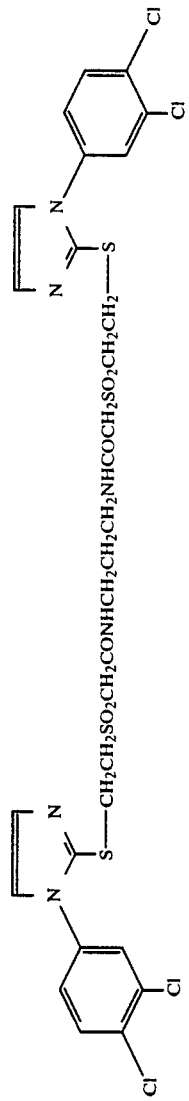

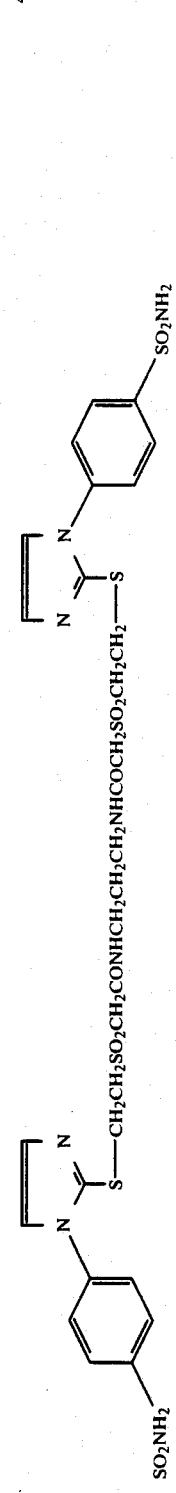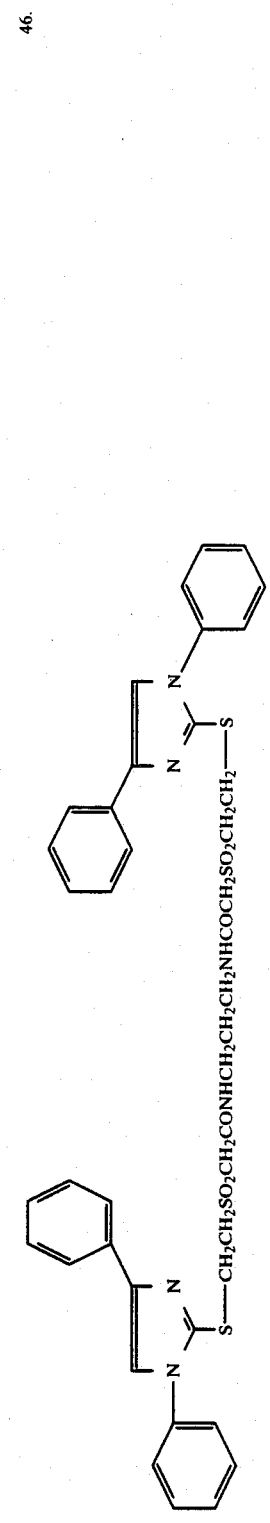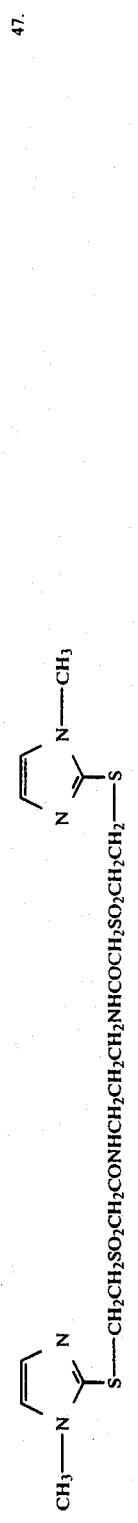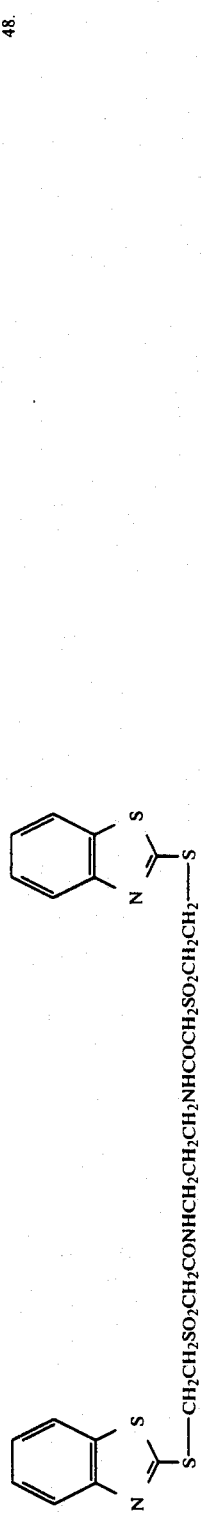

49. 
50. 
51. 
52. 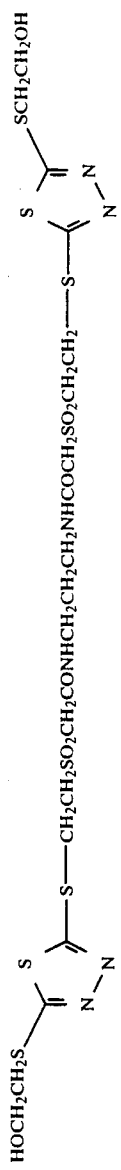
53. 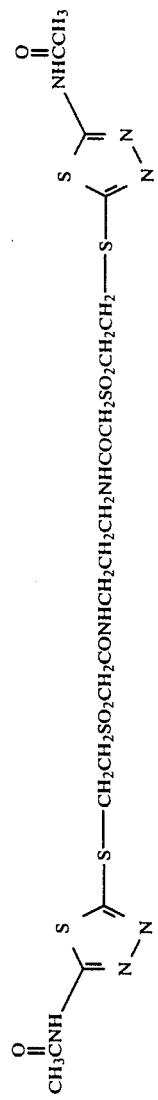
54. 
55. 

-continued
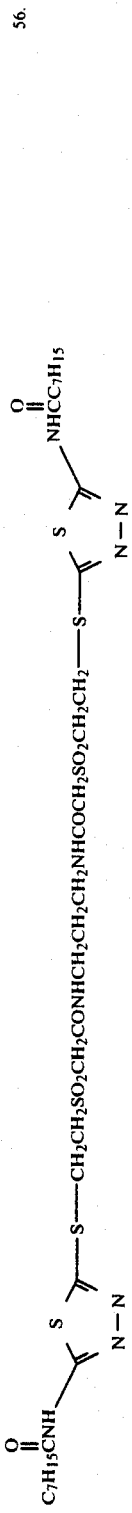
56.
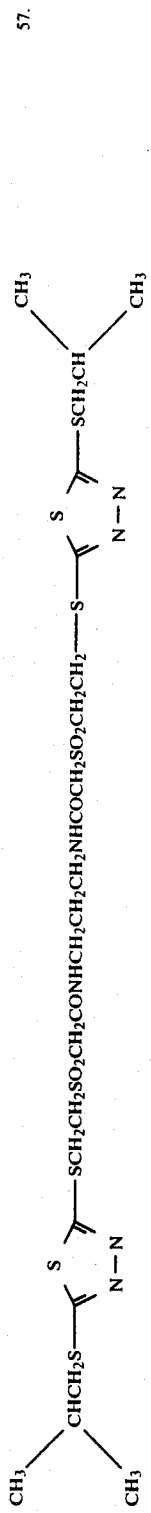
57.
58.
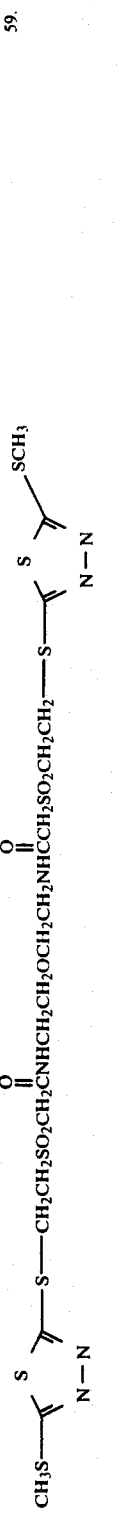
59.
60.
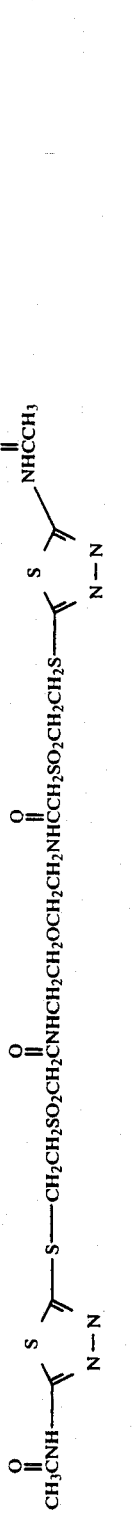
61.
62.
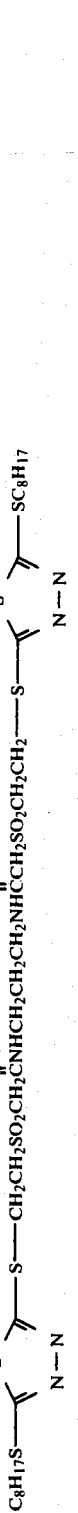
63.

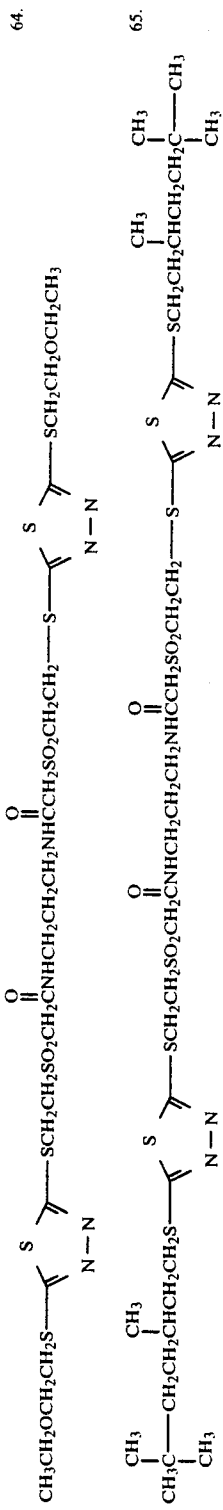

Preferred examples of the compounds represented by general formula (III) include Compounds 27, 28, 29, 30, 31, 39, 40, 41, 42, 43, 49, 50, 51, 52 and 63.

Particularly preferred examples of the compound represented by general formula (III) include Compounds 31, 39, 40, 41, 42, 43, 49, 50, 51, 52 and 63.

The compound of formula (IV) in accordance with this invention is synthesized generally by an addition reaction between a compound having at least 2 vinylsulfonyl groups per molecule as represented by general formula (IX) below and a thiol represented by general formula (X).

$$CH_2=CH-SO_2 \fbox{$CH_2$}_p \underset{\underset{(L)_n}{|}}{C}H-X^1 \quad \text{(IX)}$$
$$\overset{R^{14}}{|}$$
$$CH_2=CH-SO_2 \fbox{$CH_2$}_q \underset{\underset{R^{24}}{|}}{C}H(X^2)_m$$

In the formula, L, $X^1$, $X^2$, $R^{14}$, $R^{24}$, p, q, n and m as defined in general formula (III).

$$\underset{H}{\overset{A^2 \diagdown Y}{\underset{B^1 \diagup N}{\Bigg)}}}=S \rightleftharpoons \overset{A^2 \diagdown Y}{\underset{B^1 \diagup N}{\Bigg)}}-SH \quad \text{(X)}$$

In the formulae, Y, $A^2$, and $B^1$ are as defined in general formula (IV). Compounds having at least two vinylsulfonyl groups per molecule as the compounds of general formula (IX) are well known as a hardening agent for a gelatin binder in the photographic industry. Methods of synthesizing these compounds are described in detail, for example, in Japanese Patent Publication No. 35807/75 (corresponding to U.S. Pat. No. 3,868,257), Japanese Patent Application (OPI) Nos. 41221/78 (correspnding to U.S. Pat. No. 4,137,082) and 30022/79 and U.S. Pat. No. 3,642,486.

Compounds of general formula (I) in which B is a metal are described in Japanese Patent Application (OPI) No. 38039/72, and can be synthesized in accordance with the disclosure of this patent document.

The compounds described, for example, in Japanese Patent Application (OPI) No. 38038/72 can also be used as the image stabilizing agent precursor in accordance with this invention.

Typical examples of synthesizing compounds of formula (IV) in accordance with this invention are shown below. Those compounds of formula (IV) which are not exemplified below can be synthesized substantially in accordance with these examples. Unless otherwise indicated, all parts, percents, ratios and the like are by weight.

SYNTHESIS EXAMPLE 1

Synthesis of Compound 31

3.4 g of 3-phenyl-2,3-dihydroimidazole-2-thione, 3.3 g of 1,3-bis(vinylsulfonylacetamido)propane, 1.6 g of sodium acetate and 40 ml of acetic acid were heated with stirring at 80° C. for 10 hours.

The reaction mixture was poured into 300 ml of water, and it was extracted with two 200 ml portions of ethyl acetate. The extracts were dried over anhydrous sodium sulfate and then the solvent was evaporated. The residue was purified twice by silica gel column chromatography (a 9:1 mixture of ethyl acetate and methanol was used as a solvent in the first purification and acetonitrile was used as a solvent in the second purification) to give 1.2 g of compound 31 as a colorless resinous solid.

SYNTHESIS EXAMPLE 2

Synthesis of Compound 49

3.1 g of 2-mercapto-5-methylthio-1,3,4-thiadiazole, 3.2 g of 1,3-bis(vinylsulfonylacetamido)propane, 1.5 g of sodium acetate and 38 ml of acetic acid were heated at 80° C. for 10 hours with stirring. The reaction mixture was poured into 300 ml of ice water. The precipitated solid was collected by filtration, and recrystallized from acetonitrile to obtain 1.2 g of Compound 49 as white crystals having a melting point of 152° to 154° C.

SYNTHESIS EXAMPLE 3

Synthesis of Compound 51

4.68 g of 2-mercapto-5-hexylthio-1,3,4-thiadiazole, 3.38 g of 1,3-bis(vinylsulfonylacetamido)propane, 1.64 g of sodium acetate and 50 ml of acetic acid were heated at 80° C. for 5 hours with stirring. The reaction mixture was poured into 300 ml of ice water. The precipitated solid was collected by filtration, and recrystallized from acetone and then from a mixture of ethanol and acetonitrile to give compound 51 as white crystals having a melting point of 142° to 143° C.

SYNTHESIS EXAMPLE 4

Synthesis of Compound 50

4.12 g of 2-mercapto-5-butylthio-1,3,4-thiadiazole, 3.38 g of 1,3-bis(vinylsulfonylacetamido)propane, 1.64 g of sodium acetate and 50 ml of acetic acid were heated at 80° C. for 4.5 hours with stirring. The reaction mixture was poured into 200 ml of ice water. The precipitated solid was collected by filtration, and recrystallized twice from acetone to give compound 50 as white crystals having a melting point of 130° to 131° C.

SYNTHESIS EXAMPLE 5

Synthesis of Compound 63

5.24 g of 2-mercapto-5-octylthio-1,3,4-thiadiazole, 3.38 g of 1,3-bis(vinylsulfonylactamido)propane, 1.64 g of sodium acetate and 50 ml of acetic acid were heated at 80° C. for 5 hours with stirring. The reaction mixture was poured into 200 ml of ice water. The precipitated solid was collected by filtration, and recrystallized from acetone to give Compound 63 as white crystals having a melting point of 145° to 146° C.

SYNTHESIS EXAMPLE 6

Synthesis of Compound 52

4.0 g of 2-mercapto-5-(2-hydroxyethyl)thio-1,3,4-thiadiazole, 3.4 g of 1,3-bis(vinylsulfonylacetamido)propane, 1.64 g of sodium acetate and 50 ml of acetic acid were heated at 80° C. for 10.5 hours with stirring. The reaction mixture was poured into 200 ml of ice water. The precipitated solid was collected by filtration, and recrystallized from acetonitrile to give compound 52 as white crystals having a melting point of 115° to 119° C.

SYNTHESIS EXAMPLE 7

Synthesis of Compound 57

Acetic acid (50 ml) was added to 4.12 g of 2-(2-methylpropylthio)-5-mercapto-1,3,4-thiadiazole and 1.64 g of sodium acetate, and the mixture was heated to form a solution. To the solution was added 3.38 g of 1,3-bis(vinylsulfonylacetamido)propane, and the mixture was heated at 80° C. for 5 hours with stirring. The reaction mixture was poured into 200 ml of ice water. The resulting solid was collected by filtration and dissolved in acetonitrile. The insoluble portion was removed by filtration, and the solution was cooled. The precipitated crystals were collected by filtration. The amount of the crystals yielded was 2.8 g, and the crystals had a melting point of 106° to 110° C.

SYNTHESIS EXAMPLE 8

Synthesis of Compound 65

Acetic acid (50 ml) was added to 5.81 g of 2-mercapto-5-(3,6,6-trimethylheptylthio)-1,3,4-thiadiazole and 1.64 g of sodium acetate, and the mixture was heated to form a solution. To the solution was added 3.38 g of 1,3-bis(vinylsulfonylacetamido)propane, and the mixture was heated at 80° C. for 5 hours with stirring. The reaction mixture was poured into 200 ml of ice water. The resulting solid was collected by filtration, and recrystallized twice from ethanol. The amount of the crystals obtained was 3.4 g, and they had a melting point of 93° to 95.5° C.

The image-receiving element used in this invention has an image-receiving layer containing a silver precipitating agent, and preferably has an alkali neutralization layer, a timing layer and an image-receiving layer containing a silver precipitating agent on a support. More preferably, the alkali neutralization layer, the timing layer and the image receiving layer containing a silver precipitating agent are formed in this sequence on the support. A photosensitive element may be supported on the same support as that of the image-receiving layer. In a preferred embodiment, the photosensitive element and the image-receiving layer are supported on separate supports.

The image stabilizing agent precursor may be included in any of the layers of the image-receiving element. However, it is preferably included in a layer other than the image-receiving layer containing a silver precipitating agent. In the above image-receiving element comprising an alkali neutralization layer, a timing layer and an image-receiving layer containing a silver precipitating agent, the image stabilizing agent precursor is preferably included in the alkali neutralization layer and/or the timing layer. In the above layer construction, even when a hydrophilic polymer layer is included between the timing layer and the image-receiving layer, it is preferred to include the image stabilizing agent precursor in the alkali neutralization layer and/or the timing layer. The timing layer contains a cellulose ester (such as cellulose diacetate) to be described hereinbelow.

A method of forming an image by the silver salt diffusion transfer process is well known in the art, and its details are described, for example, in A. Rott and E. Weyde, "Photographic Silver Diffusion Transfer Process", (Focal Press, London, 1972), and Neblette, "Handbook of Photography and Reprography", Chapter 12 (7th Edition, Van Nostrand Reinhold Company, 1977). These publications describe various photographic materials used in the silver salt diffusion process. It has been found that by including the image stabilizing agent precursor in accordance with this invention in a layer of the image-receiving element which is different from the image-receiving layer containing a silver precipitating agent, discoloration of a silver image obtained by development is prevented and the performance of the image-receiving element is not affected by storage before development, so that upon development, a silver image having a sufficient optical density can be formed. This advantage is presumably due to the fact that the image stabilizing agent precursor is decomposed by the alkali in the developer during the developing treatment to form an image stabilizing agent which is diffusible and has the activity of preventing discoloration of a silver image, but that before the development, no diffusible image stabilizer having a development inhibiting action exists.

The present invention is useful in various photographic materials used in the aforesaid silver salt diffusion transfer process. Particularly preferred embodiments of the invention will be described in detail hereinbelow with regard to a material in which a photosensitive element and an image-receiving element are supported on separate supports.

Typically, at least one silver halide is present in a photosensitive layer used in this invention. Examples of such silver halides are silver chloride, silver bromide and silver iodide and silver chlorobromide, silver chloroiodide bromide and silver iodobromide, i.e. their mixtures. The silver halide is dispersed in a suitable protective colloid, such as gelatin, agar, albumin, casein, collodion, a cellulose-type substance such as carboxymethyl cellulose, a vinyl polymer such as polyvinyl alcohol or a linear polyamide such as polyhexamethyleneadipamide. Suitable emulsion for this application can be prepared by using the methods described in P. Glafkides, *Chimie et Physique Photographique*, (Paul Montel, 1967); G. F. Duffin, *Photographic Emulsion Chemistry* (The Focal Press, 1966); and V. L. Zelikman et al., Making and Coating Photographic Emulsion, (The Focal Press, 1964). Specifically, they may be prepared by the acid method, the neutral method, or the ammonia method. The mode of reacting a soluble silver salt with a soluble halogen salt may be a single jet mixing method, a double jet mixing method, or a combination of these.

A method of forming particles in the presence of an excess of a silver ion (The "reverse" mixing method) can also be used. As one type of the double jet mixing method, a method involving maintaining at a constant value the pAg of a liquid phase in which the silver halide is formed, i.e. a so-called controlled double jet method may also be used.

The silver halide emulsion may be a primitive emulsion not chemically sensitized, but usually, it is chemically sensitized. For chemical sensitization, the methods described in the above-cited books of Glafkides, Duffin and Zellikman, and *Grundlagen der Photographischen Prozesse mit Silberhalogenid-emulsionene*, (edited by H. Prieser, Akademische Verlaggesellschaft, 1968) many be used.

As required, the silver halide emulsion can be subjected to spectral sensitization or super-sensitization with one or more of cyanine dyes such as cyanine, merocyanine and carbocyanine or with a combination of a cyanine dye and a styryl dye, etc. Techniques of such color sensitization are old in the art, and are described, for example, in U.S. Pat. Nos. 2,493,748, 2,519,001, 2,688,545, 2,912,329, 2,977,229, 3,397,060, 3,480,434, 3,511,646, 3,522,052, 3,527,641, 3,615,613, 3,615,632, 3,617,295, 3,635,721, 3,615,635, 3,628,964, 3,672,897, 3,694,217 and 3,703,377, British Pat. Nos. 1,137,580, 1,195,302, 1,216,203, and 1,242,588, West German Patent Application (OLS) Nos. 2,030,326 and 2,121,780, Japanese Patent Publication Nos. 4936/68, 10773/68, and 14030/69. The selection of the techniques can be determined according to the purpose and use of the photographic material, for example, the wavelength region to be sensitized, and the desired sensitivity.

The silver halide emulsion can contain a coating aid. The coating aids described in "Coating Aids", at page 108, Vol. 92 of Product Licensing Index can be used.

The silver halide photographic emulsion may also contain an antistatic agent, a plasticizer, a fluorescent bleaching agent, an air antifogging agent, etc.

In the silver halide emulsion used in this invention, the vehicles described in "Vehicles" at page 108, Vol. 92 of *Product Licensing Index* (December 1971) may be used.

The silver halide emulsion is coated on a support together with other photographic layers as required. The methods of coating described in "Coating Procedures" at page 109, Vol. 92 of *Product Licensing Index* can be used, and the supports described in "Supports" at page 108, Vol. 92 of *Product Licensing Index* can be used.

For the purpose of increasing sensitivity and contrast or promoting development, the photographic emulsion in accordance with this invention may contain polyalkylene oxides or their derivatives such as ethers, esters or amines, thioether compounds, thiomorpholines, quaternary ammonium salts, urethane derivatives, urea derivatives, imidazole derivatives and 3-pyrazolidones. For example, the compounds described in U.S. Pat. Nos. 2,400,532, 2,423,549, 2,716,062, 3,617,280, 3,772,021, and 3,808,003 may be used.

Water-soluble dyes may be included in the photographic emulsion layer or another hydrophilic colloid layer of the photographic material prepared in accordance with this invention as filter dyes or for preventing irradiation or otherwise. The dyes include oxonol dyes, hemioxonol dyes, styryl dyes, merocyanine dyes, cyanine dyes and azo dyes. Of these, oxonol dyes, hemioxonol dyes and merocyanine dyes are useful. The dye may be mordanted in a specific layer by a cationic polymer such as a dialkylaminoalkyl acrylate.

When a dye or an ultraviolet absorber is included in the hydrophilic colloid layer in the photographic material prepared in accordance with this invention, it may be mordanted with the cationic polymer. For example, the polymers described in British Pat. No. 685,475, U.S. Pat. Nos. 2,675,316, 2,839,401, 2,882,156, 3,048,487, 3,184,309 and 3,445,231, West German Patent Application (OLS) No. 1,914,362 and Japanese Patent Application (OPI) Nos. 47624/75 and 71332/75 can be used.

The processing composition used in this invention contains a developing agent, a solvent for the silver halide and an alkali agent. If desired, the developing agent and/or the solvent for the silver halide may be included in the photosensitive element and/or the image-receiving element.

Suitable silver halide developing agents include benzene derivatives in which at least two hydroxyl and/or amino groups are substituted at the ortho- or para-position of the benzene ring, such as hydroquinone, amidol, Metol, chrysin, p-aminophenol and pyrogallol; and hydroxylamines, particularly primary and secondary aliphatic and aromatic N-substituted or beta-hydroxylamines which are soluble in aqueous alkalis and include, for example, hydroxylamine, N-methylhydroxylamine, N-ethylhydroxylamine, the hydroxylamines described in U.S. Pat. No. 2,857,276, the N-alkoxyalkylsubstituted hydroxylamines described in U.S. Pat. No. 3,293,034. The hydroxylamine derivatives having a tetrahydrofurfuryl group described in Japanese Patent Application (OPI) No. 88521/74 can also be used.

The aminoreductones described in West German Patent Application (OLS) Nos. 2,009,054, 2,009,055 and 2,009,078, and the heterocyclic aminoreductones described in U.S. Pat. No. 4,128,425 can also be used.

The tetraalkylreductic acids described in U.S. Pat. No. 3,615,440 can also be used.

A phenidone, a p-aminophenol and ascorbic acid may be used as auxiliary developers in combination with the aforesaid developing agents.

Suitable solvents for silver halides include ordinary fixing agents such as sodium thiosulfate, sodium thiocyanate, ammonium thiosulfate and the fixing agents described in the above-cited U.S. Pat. No. 2,543,181; and combinations of cyclic imides and nitrogen bases, for example a combination of a barbiturate or uracil with ammonia or an amine and the combinations described in U.S. Pat. No. 2,857,274. 1,1-bis(sulfonylalkanes) and their derivatives are also known and can be used as the solvent for silver halide in this invention.

The processing composition contains alkalis, preferably hydroxides of alkali metals such as sodium hydroxide or potassium hydroxide. If the processing composition is applied by distributing it as a thin layer between the superimposed light-sensitive element and image-receiving element in the superimposed state, and particularly distributing it such that these elements are in a superimposed relation, the processing composition preferably contains a polymeric film-forming agent, a concentrating agent or a thickener. Hydroxyethyl cellulose and sodium carboxy methyl cellulose are especially useful for this purpose. They are included in the processing composition in concentrations which provide a suitable viscosity in accordance with the known theory of the diffusion transfer photographic process. The processing composition may further contain other adjuvants known in the silver transfer process, such as an antifoggant, a toning agent or a stabilizer.

Mercapto compounds, imidazole compounds, indazole compounds and triazole compounds are useful as antifoggants and toning agents, and the compounds described in U.S. Pat. Nos. 3,565,619, 3,642,473 and 3,756,825, British Pat. No. 1,122,158 and West German Patent Application (OLS) No. 1,804,365 are especially effective. It has been found that inclusion of an oxyethylamino compound such as triethanolamine as a stabilizer is particularly useful for increasing the storage life of the processing composition, as described in U.S. Pat. No. 3,619,185.

As stated hereinabove, the image-receiving element of this invention comprises a support for supporting the image-receiving layer containing a silver precipitating agent in a hydrophilic polymer binder.

Many examples of the hydrophilic polymer are known. Regenerated cellulose is especially suitable. To prepare such an image-receiving element, there can be used a method which comprises including a silver precipitating agent in a cellulose ester such as cellulose diacetate by deposition, coating it on a support and then hydrolyzing the coated layer in the presence of alkali; a method which comprises reacting, for example, silver nitrate with sodium sulfide in a solution of a cellulose ester to form a silver precipitating agent in situ, coating the suspension on a support, and hydrolyzing the coated layer in the presence of alkali; a method which comprises hydrolyzing in the presence of alkali a cellulose ester layer coated in advance on a support and simultaneously embedding a silver precipitating agent in the hydrolyzed layer; and a method which comprises hydrolyzing a cellulose ester layer in the presence of alkali to convert it into a regenerated cellulose, and then reacting, for example, chloroauric acid with a reducing agent in the hydrolyzed layer to form a silver precipitating agent.

If desired, a layer of a non-hydrolyzed cellulose ester or a partially hydrolyzed cellulose ester may be left in the under portion of the hydrolyzed cellulose ester layer containing the silver precipitating agent, or a polymer layer such as a layer of polyvinyl butyral may be provided beneath the hydrolyzed cellulose ester layer, to serve as a waterproof layer.

In addition, if desired a second hydrophilic polymer layer may be provided between this waterproof polymeric layer and the hydrolyzed cellulose ester layer containing the silver precipitating agent. Examples of the polymer used in the second hydrophilic polymer layer include gelatin, gelatin derivatives (e.g., phthalic gelatin), saccharides (such as starch, galactomannan, gum arabic, hydroxyethyl cellulose, methyl cellulose, carboxymethyl cellulose, pullulan, and hydroxypropyl cellulose), and hydrophilic synthetic polymers (such as polyacrylamide, polymethylacrylamide, poly-N-vinylpyrrolidone, and 2-hydroxyethyl methacrylate).

Furthermore, if desired, an alkali neutralization layer may be provided, including, for example, polymer acids described in Japanese Patent Publication No. 33697/73.

In order to improve the peelability of the processing liquor, a layer of a hydrophilic polymer such as carboxymethyl cellulose, gelatin, gum arabic, a dimethylhydantoin-formaldehyde condensate or cellulose hydrogen acetate phthalate may be advantageously coated on the image-receiving layer. A fluorescent bleaching agent may be added to increase whiteness, and plasticizer is may be added to soften the polymer layer coated on the image receiving layer.

The image stabilizer agent precursor used in this invention is incorporated into at least one of the layers of the image-receiving element of this invention described above.

It has been found that in an especially preferred embodiment, the image stabilizing agent precursor is added to the layer containing the silver precipitating agent, that is, to the non-hydrolyzed cellulose ester layer beneath the image-receiving layer as described in U.S. Pat. No. 2,607,269, or to provide a hydrophilic polymer layer such as a layer of 2-hydroxyethyl methacrylate polymer beneath the hydrolyzed cellulose ester layer and add the image stabilizing agent precursor of the invention to the hydrophilic polymer layer. The amount of the image stabilizing agent precursor to be added to the non-hydrolyzed cellulose ester layer or the hydrophilic polymer layer or another layer is preferably about $1 \times 10^{-6}$ to $1000 \times 10^{-6}$ mole/m$^2$, particularly preferably $10 \times 10^{-6}$ to $500 \times 10^{-6}$ mole/m$^2$.

The image stabilizing agent precursor of the invention may be incorporated into a photographic element, by dissolving it in water or a low-boiling organic solvent such as methanol, ethanol, propanol, acetone, methyl ethyl ketone, cyclohexanone, cyclopentanone, petroleum ether, benzene, toluene, ether, tetrahydrofuran, dioxane, dimethylformamide, ethyl acetate or butyl acetate together with a suitable polymer, and coating the resulting solution. Alternatively, the photographic element may first be prepared and then immersed in a solution of the image stabilizing agent precursor.

Examples of suitable silver precipitating agents include heavy metals such as iron, lead, zinc, nickel, cadmium, tin, chromium, copper and cobalt, and noble metals such as gold, silver, platinum and palladium. Other useful silver precipitating agents are the sulfides and selenides of heavy metals, especially the sulfides of mercury, copper, aluminum, zinc, cadmium, cobalt, nickel, silver, palladium, lead, antimony, bismuth, cerium and magnesium, and the selenides of lead, zinc, antimony and nickel. The action of the silver precipitating agent in the silver transfer process is described, for example, in U.S. Pat. No. 2,774,667.

As in the prior art, the silver precipitating agent is present in a very small amount, for example about $1 \times 10^{-5}$ to $25 \times 10^{-5}$ mole/m$^2$. Usually, the lowest possible level is used, since at higher concentrations, excess silver may be deposited or an undesirable increase in background density may occur in the highlight region. A mixed silver precipitating agent may also be used. Such an image-receiving layer is substantially colorless and substantially transparent with respect to the presence of a precipitating agent.

The present invention is explained in greater detail by reference to the following examples, but the present invention should not be construed as being limited thereto.

EXAMPLE 1

(1) Preparation of an image-receiving element (A)

A solution of 12 g of cellulose diacetate (the degree of acetylation 54%) and 8 g of a 1:1 copolymer of methyl vinyl ether and maleic anhydride was coated on polyethylene laminate paper (basis weight 150 g/m$^2$, thickness of the polyethylene layer 20 microns) in which the polyethylene had been subjected to a corona discharge treatment. The total amount of cellulose diacetate and the copolymer coated was 5 g/m$^2$.

Image-receiving sheets A-1 to A-15 were prepared in the following manner.

A solution of 20 g of cellulose diacetate in 200 ml of acetone, 20 ml of methanol and each of the following image stabilizing agent precursors was prepared, and was coated on top of the above polymer layer. The amount of cellulose diacetate coated was 4 g/m$^2$, and the amount of image stabilizing agent precursor was $2 \times 10^{-4}$ mol/m$^2$.

The image stabilizing agent precursors used were as follows:

| | | |
|---|---|---|
| Image-receiving element A-1: | Compound 31 | (invention) |
| Image-receiving element A-2: | Compound 39 | (invention) |
| Image-receiving element A-3: | Compound 40 | (invention) |
| Image-receiving element A-4: | Compound 41 | (invention) |
| Image-receiving element A-5: | Compound 42 | (invention) |
| Image-receiving element A-6: | Compound 43 | (invention) |
| Image-receiving element A-7: | Compound 47 | (invention) |
| Image-receiving element A-8: | Compound 50 | (invention) |
| Image-receiving element A-9: | Compound 51 | (invention) |
| Image-receiving element A-10: | Compound 52 | (invention) |

-continued

| | | |
|---|---|---|
| Image-receiving element A-11: | Compound 63 | (invention) |
| Image-receiving element A-12: | Compound 25 | (invention) |
| Image-receiving element A-13: | 1-phenyl-2-mercapto-imidazole | (comparison) |
| Image-receiving element A-14: | 2-methylthio-5-mercapto-1,3,4-thiadiazole | (comparison) |
| Image-receiving element A-15: | No precursor added | (comparison) |

On top of this layer was further coated a solution of 10 g of cellulose diacetate in 800 ml of acetone. The amount of the coated cellulose diacetate was 3 g/m².

On top of the cellulose diacetate layer so prepared was coated an alkaline hydrolyzing solution containing a silver precipitating agent as described below at a rate of 30 ml/m² to prepare Image-receiving sheets A-1 to A-15 for a diffusion transfer process.

The alkaline hydrolyzing solution used was prepared by the following procedure.

Nickel nitrate (0.7 g) was dissolved in 7 ml of water, and the solution was added to 100 g of glycerol. With vigorous stirring, a solution of 5 g of sodium sulfide in 5 ml of water was added to this solution to prepare a silver precipitation agent dispersion of nickel sulfide. Then, 40 g of the silver precipitating agent dispersion was added to a solution of 55 g of sodium hydroxide in 300 ml of water and 1200 ml of methanol, to form the alkaline hydrolyzing solution.

(2) Preparation of a light-sensitive layer sheet

A gelatin-dispersed silver iodobromide emulsion having an average particle diameter of 1.0 micron was prepared by double jet method. The emulsion (100 g) was taken into a pot and dissolved using a constant temperature bath at 50° C. To the solution were added 10 ml of a 1% by weight aqueous solution of 3-[5-chloro-2-{2-ethyl-3-(3-ethyl-2-benzothiazolinylidene)-propenyl}-3-benzoxazolio]propanesulfone, 4-[2-{3-ethylbenzothiazolin-2-ylidene)-2-methyl-1-propenyl}-3-benzothiazolio]propanesulfonate and 4-hydroxy-6-methyl-1,3,3a,7-tetrazaindene, 10 ml of a 1% by weight aqueous solution of 2-hydroxy-4,6-dichlorotriazine sodium salt and 10 ml of a 1% by weight aqueous solution of sodium dodecylbenzenesulfonate, and the mixture was stirred. The finished emulsion was coated to a dry thickness of 5 microns on a polyethylene terephthalate film base containing titanium oxide in an amount of 10% by weight based on the weight of polyethylene telephthalate, on which a subbing layer was coated, and dried. The amount of silver coated was 1.0 g/m².

(3) Composition of a processing solution

| | |
|---|---|
| Potassium hydroxide (40% aqueous KOH solution) | 323 ml |
| Titanium dioxide | 3 g |
| Hydroxyethyl cellulose | 79 g |
| Zinc oxide | 9.75 g |
| N,N—bis-methoxyethylhydroxylamine | 75 g |
| Triethanolamine solution (composed of 6.2 parts of water and 4.5 parts of triethanolamine) | 17.14 g |
| Tetrahydropyrimidinethione | 0.4 g |
| 2,4-Dimercaptopyrimidine | 0.35 g |
| Uracil | 80 g |
| Water | 1193 g |

(4) Development and measurement of density

The photosensitive layer sheet was exposed through an optical wedge using a sensitometer having a light source with a color temperature of 5400° K. The exposed photosensitive layer sheet and the image-receiving layer sheet were superimposed, and the processing solution was spread between the sheets in a thickness of 0.05 mm to transfer and develop the image, and after standing in an atmosphere at 25° C. for 30 seconds, the sheets were peeled apart to form a positive image.

The density of the image was measured using a TCD-type self-recording densitometer (made by Fuji Film Co., Ltd.), and the maximum density ($D_{max}$) was determined, as indicated in Table 1.

(5) Accelerated degradation test (a) Accelerated degradation test on an undeveloped sample Undeveloped image-receiving elements A1–A15, exposed as described above were allowed to stand at 50° C. and 80% RH, and at 60° C. in a dry condition, respectively, for 72 hours, and were then developed in the same way as in (4) above.

(b) Accelerated discoloration test on a transferred image

The transferred image obtained by development of image receiving elements A1–A15 in the same manner as in (4) above was allowed to stand at 60° C. and 70% RH and 40° C. and 90% RH, respectively, for 72 hours, and the resulting image discoloration was evaluated, as indicated in Table 1.

(6) Results

The results of the above experiments are summarized in Table 1, which indicates $D_{max}$ and the colors of the transferred images obtained.

TABLE 1

| Image-receiving element | Maximum density (Dmax) | | | | | Color of the image after development | Color of the image after 3 days accelerated degradation test at 60° C. and 70% RH |
|---|---|---|---|---|---|---|---|
| | Immediately after development | | | After 3 day accelerated degradation test on the transferred image | | | |
| | Immediately after production | After 3 day accelerated degradation test | | | | | |
| | | 50° C., 80% RH | 60° C., Dry | 60° C., 70% RH | 40° C., 90% RH | | |
| A-1 | 1.62 | 1.58 | 1.61 | 1.43 | 1.50 | Black | Black |
| A-2 | 1.63 | 1.59 | 1.62 | 1.44 | 1.52 | " | " |
| A-3 | 1.63 | 1.59 | 1.62 | 1.44 | 1.53 | " | " |
| A-4 | 1.64 | 1.60 | 1.63 | 1.45 | 1.53 | " | " |
| A-5 | 1.66 | 1.64 | 1.65 | 1.44 | 1.52 | " | " |
| A-6 | 1.65 | 1.63 | 1.64 | 1.44 | 1.53 | " | " |
| A-7 | 1.72 | 1.69 | 1.70 | 1.38 | 1.47 | " | " |

TABLE 1-continued

| | | Maximum density (Dmax) | | | | | |
|---|---|---|---|---|---|---|---|
| | | Immediately after development | | | | | |
| | | After 3 day accelerated degradation test | | After 3 day accelerated degradation test on the transferred image | | | Color of the image after 3 days accelerated |
| Image-receiving element | Immediately after production | 50° C., 80% RH | 60° C., Dry | 60° C., 70% RH | 40° C., 90% RH | Color of the image after development | degradation test at 60° C. and 70% RH |
| A-8 | 1.66 | 1.63 | 1.65 | 1.46 | 1.54 | " | " |
| A-9 | 1.66 | 1.64 | 1.65 | 1.45 | 1.53 | " | " |
| A-10 | 1.62 | 1.58 | 1.60 | 1.46 | 1.54 | " | " |
| A-11 | 1.67 | 1.65 | 1.66 | 1.44 | 1.52 | " | " |
| A-12 | 1.60 | 1.57 | 1.60 | 1.41 | 1.51 | " | " |
| A-13 | 1.50 | 1.13 | 1.38 | 1.29 | 1.35 | " | " |
| A-14 | 1.55 | 1.11 | 1.40 | 1.36 | 1.40 | Neutral gray | Neutral gray |
| A-15 | 1.73 | 1.68 | 1.74 | 1.25 | 1.36 | Blackish brown | Yellowish brown |

The above results demonstrate that the image-receiving elements A-1 to A-12 containing the image stabilizing agent precursors in accordance with this invention have a higher maximum density immediately after processing than the comparative image-receiving elements A-13 and A-14. In the accelerated discoloration test, the decrease in maximum density for both the image-receiving elements of the invention and comparative elements A-13 and A-14 is approximately the same, while the decrease in maximum density in the accelerated degradation test is smaller in the image-receiving elements in accordance with this invention than in the comparative receiving elements. When the precursor compounds in accordance with this invention are used, the stability of the image obtained and the storability of the undeveloped sample are both remarkably superior.

While comparative samples A-13 and A-14 show an image stabilizing effect when compared with sample A-15 which does not contain any image stabilizer, the storability of the undeveloped samples was poor.

EXAMPLE 2

(1) Preparation of an image-receiving element (B)

A solution of 10 g of cellulose diacetate and 10 g of a 1:1 styrene/maleic anhydride copolymer in 200 ml of acetone was coated on the same polyethylene laminated paper as used in Example 1 to a dry film thickness of 5 microns.

Image-receiving sheets B-1 to B-15 were prepared in the following manner.

10 g of cellulose diacetate was dissolved in a mixed solvent of 180 ml of acetone and 20 ml of methanol, to which each of the image stabilizing agent precursors B-1–B-15 shown below was added. The resulting solutions were coated to a dry film thickness of 4 microns on the coated layer of the sheets prepared above.

The amount of image stabilizing agent precursor coated was $2 \times 10^{-4}$ mol/m$^2$.

The image stabilizing agent precursors used were as follows.

| | | |
|---|---|---|
| Image-receiving element B-1: | Compound 31 | (invention) |
| Image-receiving element B-2: | Compound 39 | (invention) |
| Image-receiving element B-3: | Compound 40 | (invention) |
| Image-receiving element B-4: | Compound 41 | (invention) |
| Image receiving element B-5: | Compound 42 | (invention) |
| Image receiving element B-6: | Compound 43 | (invention) |
| Image-receiving element B-7: | Compound 49 | (invention) |
| Image-receiving element B-8: | Compound 50 | (invention) |
| Image-receiving element B-9: | Compound 51 | (invention) |
| Image-receiving element B-10: | Compound 52 | (invention) |
| Image-receiving element B-11: | Compound 63 | (invention) |
| Image-receiving element B-12: | Compound 25 | (invention) |
| Image-receiving element B-13: | 1-phenyl-2-mercapto-imidazole | (comparison) |
| Image-receiving element B-14: | 2-methylthio-5-mercapto-1,3,4-thiadiazole | (comparison) |
| Image-receiving element B-15: | No precursor added | (comparison) |

On top of the above layer was coated to a dry film thickness of 1 micron a solution of 10 g of polyacrylamide in 200 ml of water.

Furthermore, a cellulose diacetate solution containing palladium sulfide was coated on the above layer to a dry film thickness of 1 micron.

The cellulose diacetate solution containing palladium sulfide was prepared by the following procedure.

10 g of cellulose diacetate (degree of acetylation 54%) was dissolved in 160 ml of acetone and 20 ml of methanol. To the resulting solution were added with vigorous stirring a solution of 0.024 g of sodium sulfide (nonahydrate) in 10 ml of methanol and a solution of 0.03 g of sodium palladium chloride in 3 ml of water and 7 ml of methanol.

An alkaline hydrolyzing solution prepared by dissolving 40 g of potassium hydroxide in 200 ml of water and 800 ml of methanol was coated on the resulting cellulose diacetate layer containing palladium sulfide to form a regenerated cellulose layer.

(2) Preparation of light-sensitive sheets, exposure, superimposition with image-receiving elements and development were conducted as in Example 1.

(3) Testing conditions

The image-receiving elements B-1 to B-15 were tested in the same way as in Example 1.

(4) Results

The results are summarized in Table 2.

The results clearly show that the image-receiving sheets (B-1 to B-12) containing the precursor compounds in accordance with this invention have both excellent image stability and storability of the undeveloped image-receiving sheets.

TABLE 2

| Image-receiving element | Maximum density (Dmax) | | | | | Color of the image immediately after development | Color of the image after 3 days accelerated degradation test at 60° C. and 70% RH |
|---|---|---|---|---|---|---|---|
| | Immediately after development | | | After 3 day accelerated degradation test on the transferred image | | | |
| | Immediately after production | After 3 day accelerated degradation test | | | | | |
| | | 50° C., 80% RH | 60° C., Dry | 60° C., 70% RH | 40° C., 90% RH | | |
| B-1 | 1.73 | 1.70 | 1.69 | 1.58 | 1.60 | Neutral gray | Neutral gray |
| B-2 | 1.74 | 1.71 | 1.72 | 1.59 | 1.61 | " | " |
| B-3 | 1.74 | 1.71 | 1.72 | 1.59 | 1.60 | " | " |
| B-4 | 1.75 | 1.72 | 1.71 | 1.60 | 1.61 | " | " |
| B-5 | 1.77 | 1.75 | 1.75 | 1.59 | 1.60 | " | " |
| B-6 | 1.76 | 1.75 | 1.75 | 1.59 | 1.61 | " | " |
| B-7 | 1.82 | 1.80 | 1.81 | 1.53 | 1.55 | " | " |
| B-8 | 1.77 | 1.74 | 1.78 | 1.61 | 1.62 | " | " |
| B-9 | 1.77 | 1.73 | 1.75 | 1.60 | 1.62 | " | " |
| B-10 | 1.74 | 1.72 | 1.72 | 1.61 | 1.62 | " | " |
| B-11 | 1.78 | 1.76 | 1.77 | 1.59 | 1.60 | " | " |
| B-12 | 1.50 | 1.24 | 1.40 | 1.35 | 1.36 | " | " |
| B-13 | 1.55 | 1.15 | 1.41 | 1.38 | 1.40 | " | " |
| B-14 | 1.85 | 1.80 | 1.83 | 1.25 | 1.34 | Light brown | Yellowish brown |

While the invention has been described in detail and with reference to specific embodiments thereof, it will be apparent to one skilled in the art that various changes and modifications can be made therein without departing from the spirit and the scope thereof.

What is claimed is:

1. An image-receiving element for a silver salt diffusion transfer process, said element comprising an image stabilizing agent precursor having an inactive group capable of being removed upon contact with an alkaline processing composition, and substantially lacking an image-stabilizing function prior to contact with the alkaline processing composition, said image stabilizing agent precursor being represented by general formula (III):

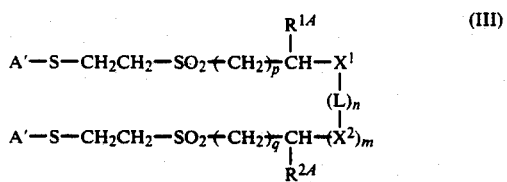

wherein A' represents a substituted or unsubstituted alkyl group, a substituted or unsubstituted aryl group or a 5- or 6-membered nitrogen-containing heterocyclic ring; $R^{1A}$ and $R^{2A}$ may be the same or different and each represents hydrogen or an alkyl group having 1 to 4 carbon atoms; p and q are each 0 or an integer of 1 to 3 and may be the same or different; $X^1$ and $X^2$ may be the same or different, and each represents an ester linkage, a substituted or unsubstituted amido linkage, or an ether linkage and L represents an alkylene group, a phenylene group or a xylylene group; and n and m are each 0 or 1, provided that when $X^1$ and $X^2$ are amido groups, substituents on the nitrogen may be linked to each other to form a hetero ring together with L and a part of each of $X^1$ and $X^2$.

2. The image-receiving element as claimed in claim 1, wherein said image stabilizing agent precursor is represented by general formula (IV):

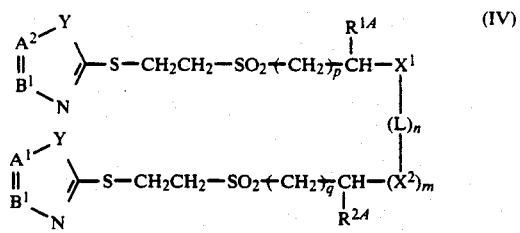

wherein $A^2$ and $B^1$ may be the same or different and each represents a carbon atom or a nitrogen atom, which may be further substituted by a subsubstituent having not more than 20 carbon atoms and when $A^2$ and $B^1$ are both carbon atoms, they may be linked through a divalent group to form an addition ring; Y represents an oxygen atom, a sulfur atom or nitrogen atom, said nitrogen atom being substituted with a substituent having not more than 20 carbon atoms; and $R^{1A}$, $R^{2A}$, $X^1$, $X^2$, m, n, p, q, and L are the same as defined in claim 1.

3. The image-receiving element as claimed in claim 2, wherein said image stabilizing agent precursor is represented by general formula (V):

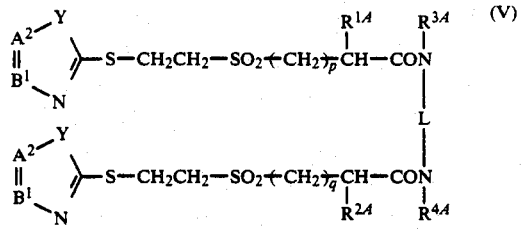

wherein Y, $A^2$, $B^1$, $R^{1A}$, $R^{2A}$, L, p and q are as defined in claim 2; $R^{3A}$ and $R^{4A}$ may be the same or different and each represents hydrogen, an alkyl group having 1 to 4 carbon atoms or a phenyl group; and $R^{3A}$ and $R^{4A}$ may be linked to each other to form a hetero ring together with L and the two nitrogen atoms.

4. The image-receiving element as claimed in claim 3, wherein said image stabilizing agent precursor is represented by general formula (VI):

5. The image-receiving element as claimed in claim 2, wherein said image stabilizing agent precursor is represented by general formula (VII):

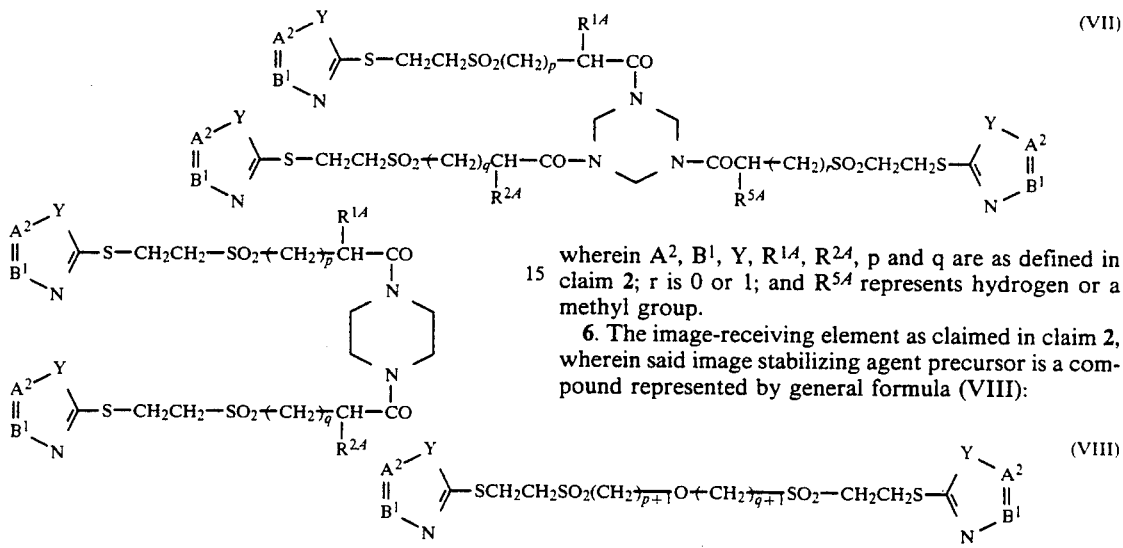

wherein $A^2$, $B^1$, Y, $R^{14}$, $R^{24}$, p and q are as defined in claim 2; r is 0 or 1; and $R^{5A}$ represents hydrogen or a methyl group.

6. The image-receiving element as claimed in claim 2, wherein said image stabilizing agent precursor is a compound represented by general formula (VIII):

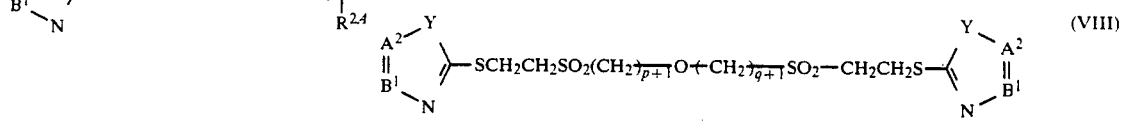

wherein $A^2$, $B^1$, Y, p and q are as defined in claim 2.

7. An image-receiving element as claimed in claim 1, wherein said image-stabilizing agent precursor is selected from the group consisting of compounds 27, 28, 29, 30, 31, 39, 40, 41, 42, 43, 49, 50, 51, 52 and 63 as set forth below:

wherein $A^2$, $B^1$, Y, $R^{14}$, $R^{24}$, p and q are as defined in claim 3.

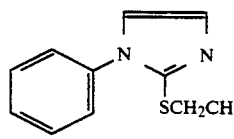 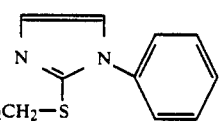

SCH$_2$CH$_2$SO$_2$CH$_2$CH$_2$CONHCH$_2$CH$_2$NHCOCH$_2$CH$_2$SO$_2$CH$_2$CH$_2$—S

27.

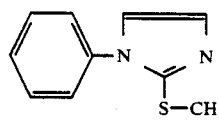 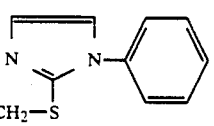

S—CH$_2$CH$_2$SO$_2$CH$_2$CH$_2$CON(C$_2$H$_5$)CH$_2$CH$_2$N(C$_2$H$_5$)COCH$_2$CH$_2$SO$_2$CH$_2$CH$_2$—S

28.

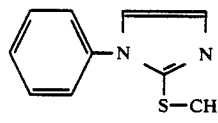 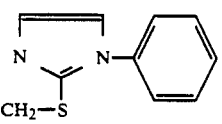

S—CH$_2$CH$_2$SO$_2$CH$_2$CH$_2$CONHCH$_2$CH$_2$CH$_2$NHCOCH$_2$CH$_2$SO$_2$CH$_2$CH$_2$—S

29.

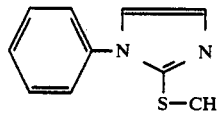 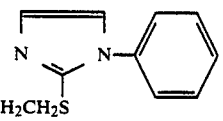

S—CH$_2$CH$_2$SO$_2$CH$_2$CONHCH$_2$CH$_2$NHCOCH$_2$SO$_2$CH$_2$CH$_2$S

30.

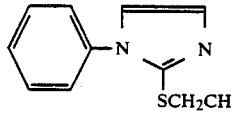 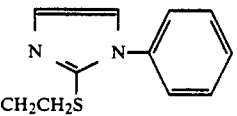

SCH$_2$CH$_2$SO$_2$CH$_2$CONHCH$_2$CH$_2$CH$_2$NHCOCH$_2$SO$_2$CH$_2$CH$_2$S

31.

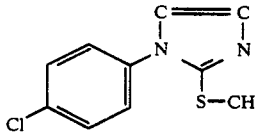 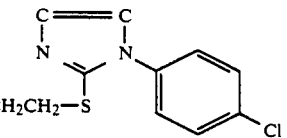

S—CH$_2$CH$_2$SO$_2$CH$_2$CH$_2$CONHCH$_2$CH$_2$CH$_2$NHCOCH$_2$CH$_2$SO$_2$CH$_2$CH$_2$—S

39.

-continued

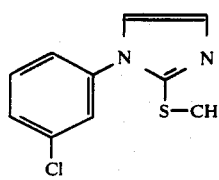—CH₂CH₂SO₂CH₂CONHCH₂CH₂CH₂NHCOCH₂SO₂CH₂CH₂—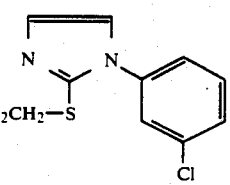   40.

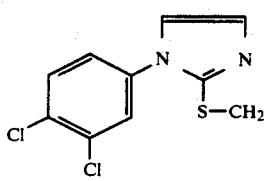—CH₂CH₂SO₂CH₂CONHCH₂CH₂CH₂NHCOCH₂SO₂CH₂CH₂—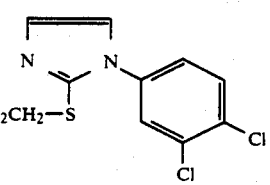   41.

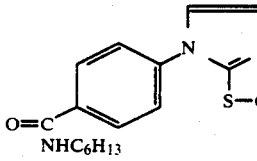—CH₂CH₂SO₂CH₂CONHCH₂CH₂CH₂NHCOCH₂SO₂CH₂CH₂—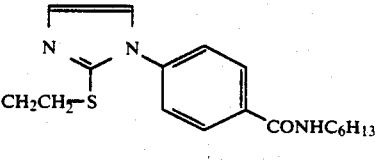   42.

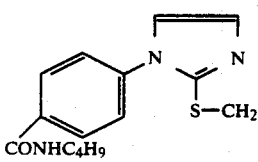—CH₂CH₂SO₂CH₂CONHCH₂CH₂CH₂NHCOCH₂SO₂CH₂CH₂—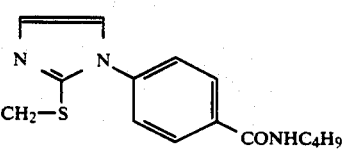   43.

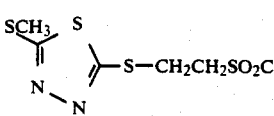—S—CH₂CH₂SO₂CH₂CONHCH₂CH₂CH₂NHCOCH₂SO₂CH₂CH₂—S—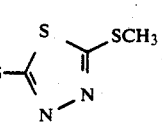   49.

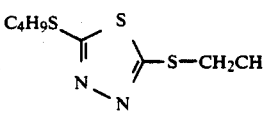—S—CH₂CH₂SO₂CH₂CONHCH₂CH₂CH₂NHCOCH₂SO₂CH₂CH₂—S—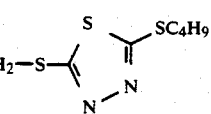   50.

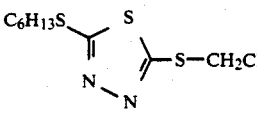—S—CH₂CH₂SO₂CH₂CONHCH₂CH₂CH₂NHCOCH₂SO₂CH₂CH₂—S—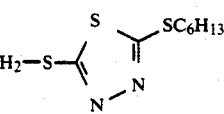   51.

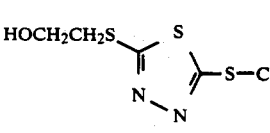—S—CH₂CH₂SO₂CH₂CONHCH₂CH₂CH₂NHCOCH₂SO₂CH₂CH₂—S—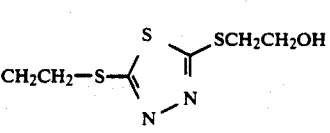   52.

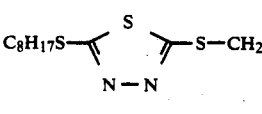—S—CH₂CH₂SO₂CH₂$\overset{\text{O}}{\overset{\|}{\text{C}}}$NHCH₂CH₂CH₂NH$\overset{\text{O}}{\overset{\|}{\text{C}}}$CH₂SO₂CH₂CH₂—S—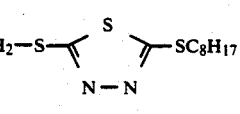   63.

8. An image-receiving element as claimed in claim 7, wherein said image stabilizing agent precursor is selected from the group consisting of Compounds 31, 39, 40, 41, 42, 43, 49, 50, 51, 52 and 63.

9. The image-receiving element as claimed in claim 1, wherein said element further comprises an alkali neutralization layer, a timing layer and an image-receiving layer comprising a silver precipitating agent.

10. The image-receiving element as claimed in claim 9, wherein said image-stabilizing agent precursor is present in at least one of the alkali neutralization layer and the timing layer.

11. The image-receiving element as claimed in claim 10, wherein said image stabilizing agent precursor is present in the timing layer.

12. The image-receiving element, as claimed in claim 1, wherein said element comprises an image-receiving layer having a silver precipitation agent.

13. The image-receiving element as claimed in claim 12, wherein said image stabilizing agent precursor is present in a layer other than the image-receiving layer containing a silver precipitating agent.

14. An image-receiving element as claimed in claim 9, wherein said element comprises a support having an alkali neutralization layer, a timing layer and an image-receiving layer containing a silver precipitating agent formed on said support in this sequence.

15. An image-receiving element as claimed in claim 14, wherein said image stabilizing agent precursor is included in the alkali neutralizing agent layer and/or the timing layer.

16. The image-receiving element claimed in claim 14, wherein said image stabilizing agent precursor is included in at least one of said alkali neutralization layer and said timing layer.

17. An image-receiving element as claimed in claim 16, wherein said image stabilizing precursor is contained in said timing layer.

18. An image-receiving element as claimed in claim 14, wherein said element further comprises a hydrophilic polymer layer between said timing layer and said image-receiving layer.

19. The image-receiving element as claimed in claim 18, wherein said image stabilizing agent precursor is contained in said timing layer.

20. The image-receiving element as claimed in claim 14, wherein said timing layer further contains a cellulose ester.

21. The image-receiving element as claimed in claim 1, wherein said image stabilizing agent precursor is present in said layer in a concentration of from about $1 \times 10^{-6}$ to $1000 \times 10^{-6}$ mol/m$^2$.

22. The image-receiving element as claimed in claim 21, wherein said image stabilizing agent precursor is present in said layer in a concentration of from about $10 \times 10^{-6}$ to about $500 \times 10^{-6}$ mol/m$^2$.

23. In a silver salt diffusion transfer process, a method for forming an image comprising the steps of imagewise exposing a silver halide photosensitive layer sheet, superimposing said photosensitive layer sheet on an image-receiving element as claimed in claim 1, and contacting said image-receiving element and said light-sensitive layer sheet with an alkaline processing solution to transfer and develop an image on said image-receiving element.

24. The image-receiving element as claimed in claim 15, wherein said timing layer further contains a cellulose ester.

25. The image-receiving element as claimed in claim 16, wherein said timing layer further contains a cellulose ester.

26. The image-receiving element as claimed in claim 17, wherein said timing layer further contains a cellulose ester.

27. The image-receiving element as claimed in claim 18, wherein said timing layer further contains a cellulose ester.

28. The image-receiving element as claimed in claim 19, wherein said timing layer further contains a cellulose ester.

* * * * *